US011266781B2

(12) United States Patent
Srinivasan et al.

(10) Patent No.: US 11,266,781 B2
(45) Date of Patent: Mar. 8, 2022

(54) PEN NEEDLE EXCHANGE SYSTEM

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US); Mohammadreza Ramezanifard, San Diego, CA (US); Stefan Gisler, Winterthur (CH)

(73) Assignee: Becton, Dickinson and Company, Franklin Lakes, NJ (US)

( * ) Notice: Subject to any disclaimer, the term of this patent is extended or adjusted under 35 U.S.C. 154(b) by 418 days.

(21) Appl. No.: 16/095,608

(22) PCT Filed: Mar. 31, 2017

(86) PCT No.: PCT/US2017/025352
§ 371 (c)(1),
(2) Date: Oct. 22, 2018

(87) PCT Pub. No.: WO2017/189169
PCT Pub. Date: Nov. 2, 2017

(65) Prior Publication Data
US 2019/0125972 A1 May 2, 2019

Related U.S. Application Data

(60) Provisional application No. 62/328,676, filed on Apr. 28, 2016.

(51) Int. Cl.
*A61M 5/20* (2006.01)
*A61M 5/172* (2006.01)
(Continued)

(52) U.S. Cl.
CPC .............. *A61M 5/20* (2013.01); *A61M 5/172* (2013.01); *A61M 5/34* (2013.01); *A61M 5/345* (2013.01);
(Continued)

(58) Field of Classification Search
CPC ........ A61M 5/172; A61M 5/34; A61M 5/345; A61M 2005/2006;
(Continued)

(56) References Cited

U.S. PATENT DOCUMENTS 5,829,589 A   11/1998  Nguyen et al.
5,873,462 A    2/1999  Nguyen et al.
(Continued)

FOREIGN PATENT DOCUMENTS

CN        104524667 A     4/2015
EP          2119423 A1   11/2009
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An electronic system (200) connectable to a medication delivery pen (4) and a needle assembly (2, 100), the electronic system (200) exchanging data regarding a medicament traveling from the medication delivery pen (4) to the needle assembly (2,100), the electronic system (200) comprising a hub (214) having a spike (216) that is configured to engage the medication delivery pen (4) and pierce a reservoir septum (6) of the medication delivery pen (4), a
(Continued)

flow sensor (220) that is in fluid communication with the hub (214) to measure flow data of the medicament, one or more circuit boards (250, 260) electrically contacting the flow sensor (220) to process and transmit the flow data, the one or more circuit hoards (250, 260) include one or more fluid path holes (256, 264) to route a flow of medicament, and a septum (270, 284) that is configured to provide fluid communication between the flow sensor (220) and one of a plurality of needles (40, 124) of the needle assembly (2, 100) to administer the medicament to a patient.

19 Claims, 24 Drawing Sheets

(51) Int. Cl.
    *G01N 11/00*     (2006.01)
    *A61M 5/34*     (2006.01)
    *A61M 5/00*     (2006.01)
    *A61M 5/14*     (2006.01)

(52) U.S. Cl.
    CPC ............... *G01N 11/00* (2013.01); *A61M 5/14* (2013.01); *A61M 2005/004* (2013.01); *A61M 2005/2006* (2013.01); *A61M 2205/3331* (2013.01); *A61M 2205/3334* (2013.01); *A61M 2205/50* (2013.01); *A61M 2205/583* (2013.01); *A61M 2205/8206* (2013.01)

(58) Field of Classification Search
    CPC ....... A61M 2005/3331–3334; A61M 2205/50; A61M 2205/583; A61M 2205/584; A61M 5/16886; A61M 5/1689; A61M 5/31533; A61M 5/31546; A61M 5/31568–3157
    See application file for complete search history.

(56) References Cited

U.S. PATENT DOCUMENTS

| | | | |
|---|---|---|---|
| 5,931,817 | A | 8/1999 | Nguyen et al. |
| 8,876,780 | B2 | 11/2014 | Bruehwiler et al. |
| 9,101,724 | B2 | 8/2015 | Chapin et al. |
| 9,107,988 | B2 | 8/2015 | Bruehwiler et al. |
| 9,155,838 | B2 | 10/2015 | Bilton et al. |
| 9,381,303 | B2 | 7/2016 | Abhijitsinh et al. |
| 9,717,860 | B2 | 8/2017 | Bruehwiler et al. |
| 10,029,042 | B2 | 7/2018 | Searle et al. |
| 2001/0014792 | A1 | 8/2001 | West et al. |
| 2002/0020646 | A1 | 2/2002 | Groth et al. |
| 2002/0020647 | A1 | 2/2002 | Groth |
| 2005/0020983 | A1 | 1/2005 | Schreijag et al. |
| 2005/0084631 | A1 | 4/2005 | Anderson |
| 2007/0112299 | A1* | 5/2007 | Smit ................ A61M 5/31566 604/67 |
| 2008/0033369 | A1 | 2/2008 | Kohlbrenner et al. |
| 2008/0312604 | A1 | 12/2008 | Boesen |
| 2009/0067989 | A1 | 3/2009 | Estes et al. |
| 2010/0217206 | A1 | 8/2010 | Lum et al. |
| 2011/0068034 | A1 | 3/2011 | Hwang et al. |
| 2011/0185821 | A1* | 8/2011 | Genosar ................ G01F 1/7046 73/861.08 |
| 2012/0004620 | A1 | 1/2012 | Spool et al. |
| 2012/0016315 | A1 | 1/2012 | Radmer et al. |
| 2012/0041373 | A1 | 2/2012 | Bruehwiler et al. |
| 2012/0041381 | A1 | 2/2012 | Raj et al. |
| 2012/0041383 | A1* | 2/2012 | Bruehwiler ........... A61M 5/008 604/192 |
| 2012/0041390 | A1 | 2/2012 | Spool et al. |
| 2013/0041321 | A1 | 2/2013 | Cross et al. |
| 2013/0053751 | A1 | 2/2013 | Holtham |
| 2014/0076758 | A1 | 3/2014 | Dasbach et al. |
| 2014/0123479 | A1 | 5/2014 | Dasbach |
| 2014/0262884 | A1 | 9/2014 | Priebe et al. |
| 2014/0299622 | A1 | 10/2014 | Hofmann et al. |
| 2014/0339113 | A1 | 11/2014 | Hofmann et al. |
| 2015/0025469 | A1 | 1/2015 | Larsen et al. |
| 2015/0163898 | A1 | 6/2015 | Mokhtarzad |
| 2015/0196707 | A1* | 7/2015 | Moore ................ A61M 5/1408 604/506 |
| 2015/0335827 | A1 | 11/2015 | Stefansen et al. |
| 2015/0346184 | A1 | 12/2015 | Galasso |
| 2016/0000992 | A1 | 1/2016 | Steel et al. |
| 2016/0030683 | A1* | 2/2016 | Taylor ..................... A61M 5/32 604/151 |
| 2016/0074587 | A1 | 3/2016 | Searle et al. |
| 2016/0082195 | A1 | 3/2016 | Atterbury et al. |
| 2016/0106925 | A1 | 4/2016 | Boesen |
| 2016/0339431 | A1* | 11/2016 | Shmilovich ....... B01L 3/502707 |
| 2018/0126088 | A1* | 5/2018 | Radmer ............ A61M 5/31583 |
| 2019/0001060 | A1* | 1/2019 | Gylleby ............ A61M 5/31568 |
| 2019/0001069 | A1* | 1/2019 | Carlsson ................ A61M 5/20 |
| 2019/0082741 | A1* | 3/2019 | Verleur ................ A24F 47/008 |

FOREIGN PATENT DOCUMENTS

| | | |
|---|---|---|
| EP | 2420270 A2 | 2/2012 |
| EP | 2586475 A1 | 5/2013 |
| EP | 2696913 B1 | 9/2015 |
| JP | 2008523930 | 7/2008 |
| JP | 2012050821 | 3/2012 |
| WO | 2008/150715 A1 | 12/2008 |
| WO | 2014/020001 A1 | 2/2014 |
| WO | 2016/050902 A1 | 4/2016 |

\* cited by examiner

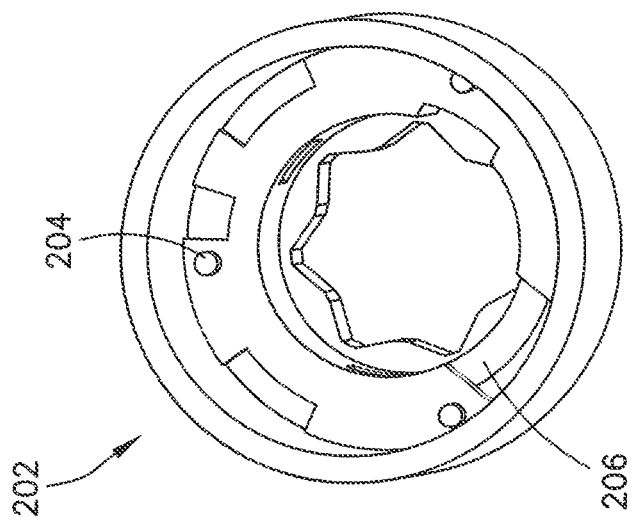
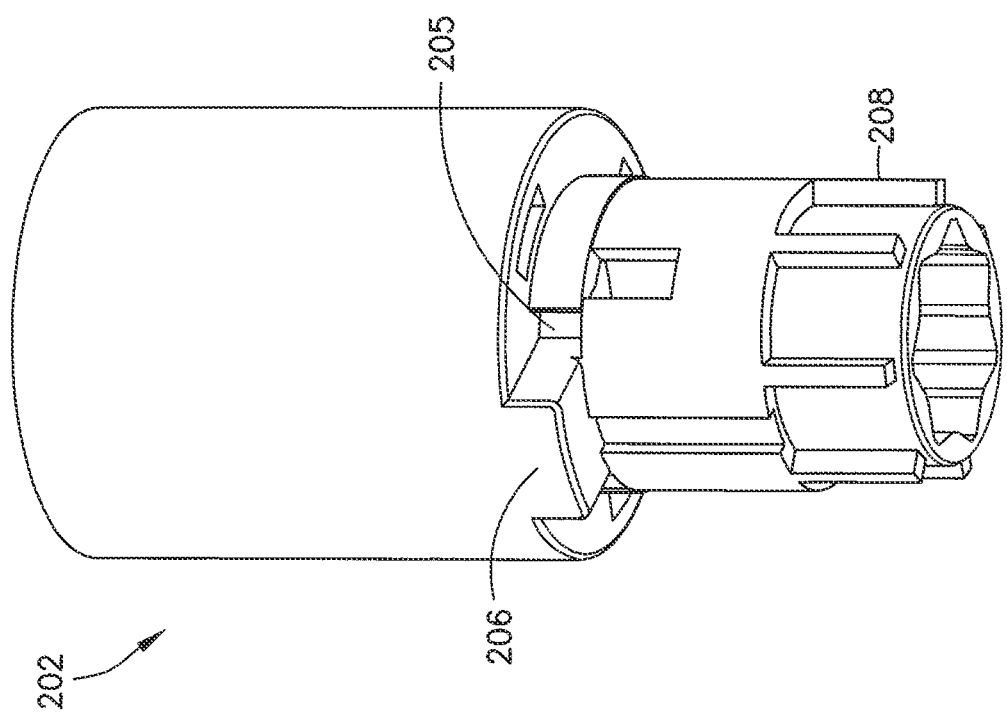

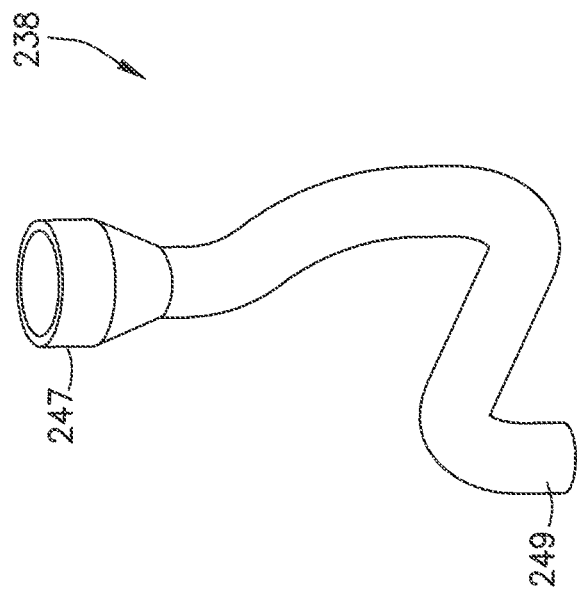
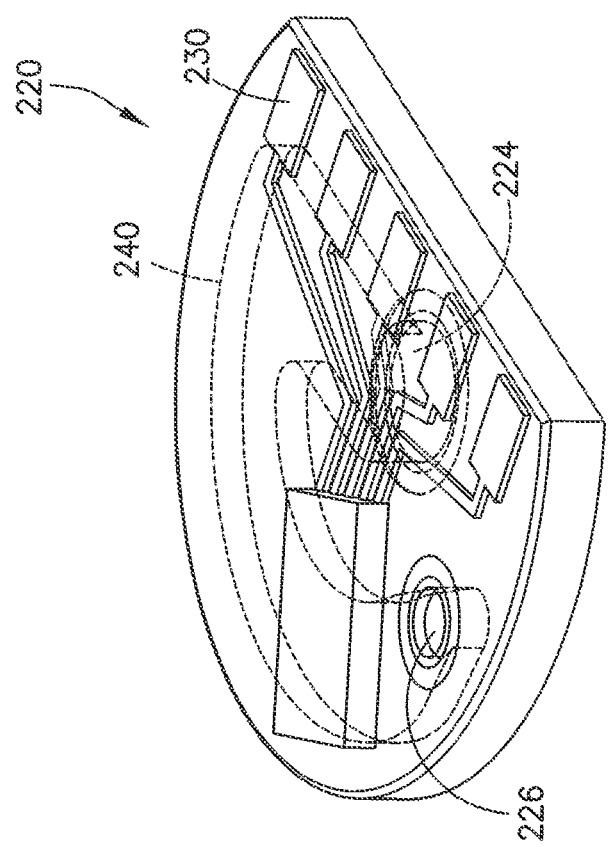

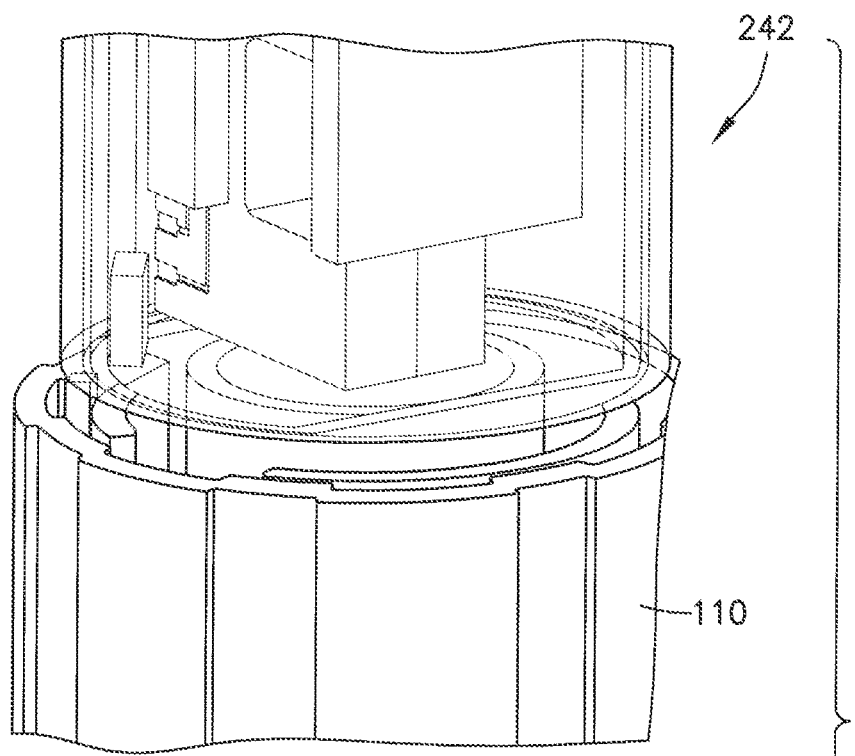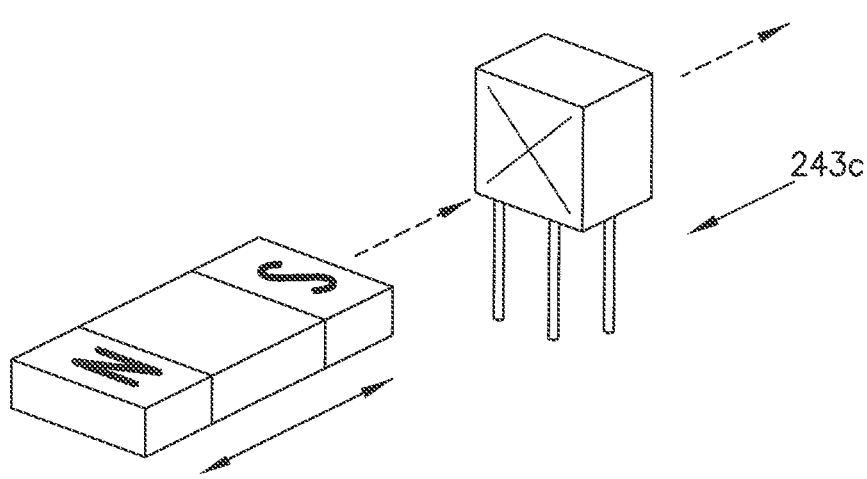
FIG. 25

PEN NEEDLE EXCHANGE SYSTEM

This application claims the benefit under 35 U.S.C. § 119(e) of U.S. Provisional Patent Application Ser. 62/328,676, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single use pen needles. A medication pen is designed for safety and sterility. However, inefficiencies and inconveniences arise.

SUMMARY OF THE INVENTION

It is an aspect of the present invention to provide an electronic exchange system that is attachable to a medication pen to analyze medicament flow and communicate medicament data. Such an electronic exchange system provides advantages in separating a patient end and a non-patient end by acting as an intermediary between the medication pen and an injection surface. The electronic exchange system also advantageously allows for engagement and disengagement to the medication pen. Moreover, electrical components of the electronic exchange system are advantageously sealed from medicament flow. Specifically, the medicament flow is strategically routed around various electrical components for system compactness, improved reliability and an improved operational interface.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an electronic system connectable to a medication delivery pen and a needle assembly, the electronic system exchanging data regarding a medicament traveling from the medication delivery pen to the needle assembly, the electronic system comprising a hub having a spike that is configured to engage the medication delivery pen and pierce a reservoir septum of the medication delivery pen, a flow sensor that is in fluid communication with the hub to measure flow data of the medicament, one or more circuit boards electrically contacting the flow sensor to process and transmit the flow data, the one or more circuit boards include one or more fluid path holes to route a flow of medicament, and a septum body that is configured to provide fluid communication between the flow sensor and one of a plurality of needles of the needle assembly to administer the medicament to a patient.

The foregoing and/or other aspects of the present invention can also be achieved by a method of operating an electronic system connectable to a medication delivery pen and a needle assembly, the electronic system exchanging data regarding a medicament traveling from the medication delivery pen to the needle assembly, the method comprising piercing a reservoir septum of the medication delivery pen with a spike enclosed in a hub, connecting the medication delivery pen to the hub, providing fluid communication between the spike and a flow sensor to measure flow data of the medicament, processing and transmitting the flow data from the flow sensor to a circuit board, and routing medicament flow from the flow sensor, through the circuit board and to a septum body for delivery of the medicament to a patient when connected to the needle assembly.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 7 illustrates a front perspective view of a hub;

FIG. 8 illustrates a top perspective view of the hub;

FIG. 11 illustrates a transparent perspective view of the flow sensor;

FIG. 12 illustrates a perspective view of a fluid conduit;

FIG. 25 illustrates an electronic exchange system including an activation switch being a hall effect sensor;

DETAILED DESCRIPTION OF EXEMPLARY EMBODIMENTS

Figure 2:
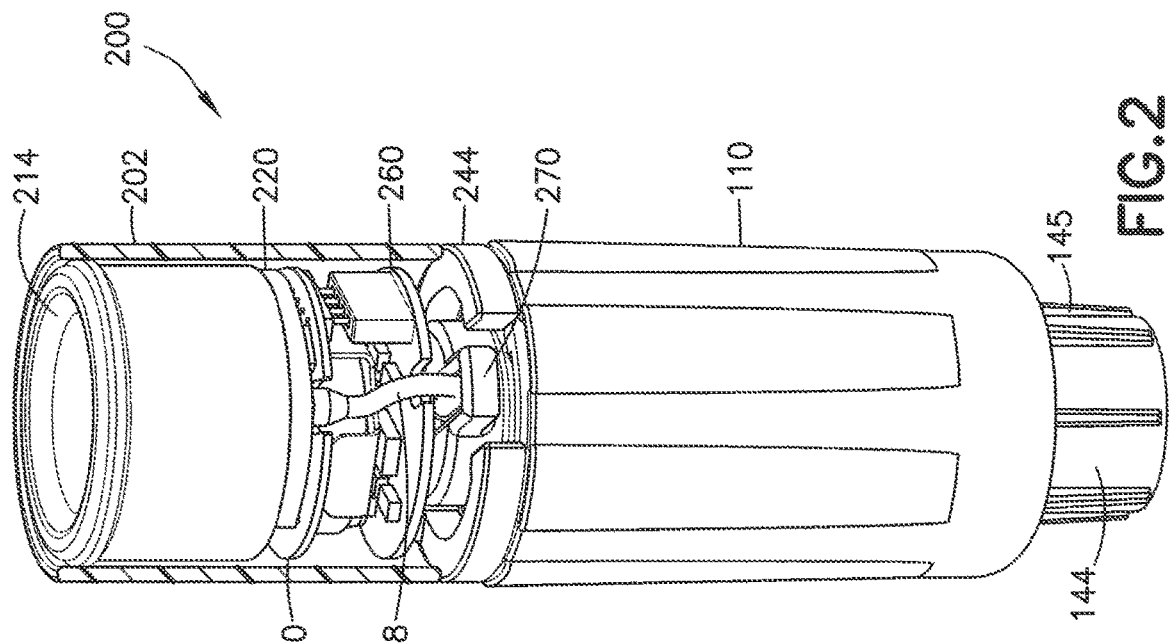
FIG. 2 illustrates the front perspective view of the electronic exchange system attached to a needle assembly of FIG. 1 with a housing removed.
Figure 1:
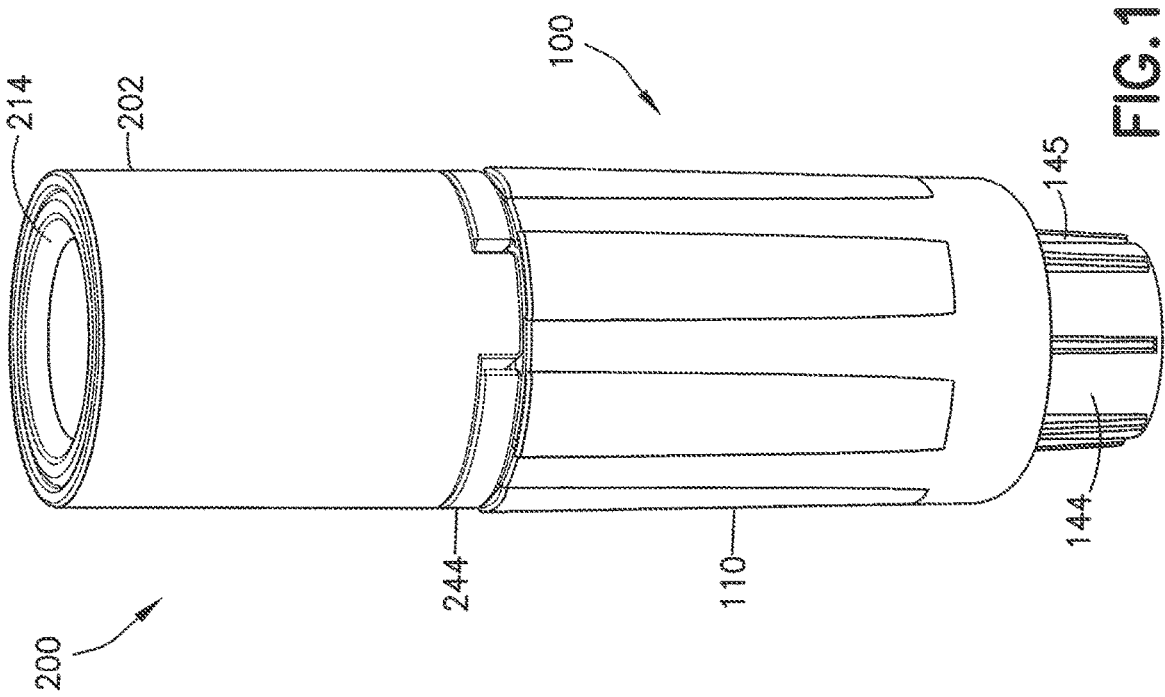
FIG. 1 illustrates a front perspective view of an exemplary electronic exchange system attached to a needle assembly.

FIGS. 1 and 2, according to one embodiment, illustrate an exemplary electronic exchange system 200 engaged to a needle assembly 100. The electronic exchange system 200 is enclosed by a housing 202 which is fixed to a hub 214. The operation of the electronic exchange system 200 is indicated via illumination of a diffuser ring 244. Additional components of the electronic exchange system 200 include a flow sensor 220, a battery board 250, a main board 260, a fluid conduit tube 238, and an upper septum 270. Further details of each of these features are described below.

The electronic exchange system 200 of FIGS. 1 and 2 is connected to an exemplary needle assembly 100. The needle assembly 101 includes a housing 110 and a bottom guide 144 including external fins 145. Further details of the needle assembly 100 are described below. Benefits and advantages of the electronic exchange system 200 cooperating with a medication delivery pen and the needle assembly 100 are described below.

Figure 3:
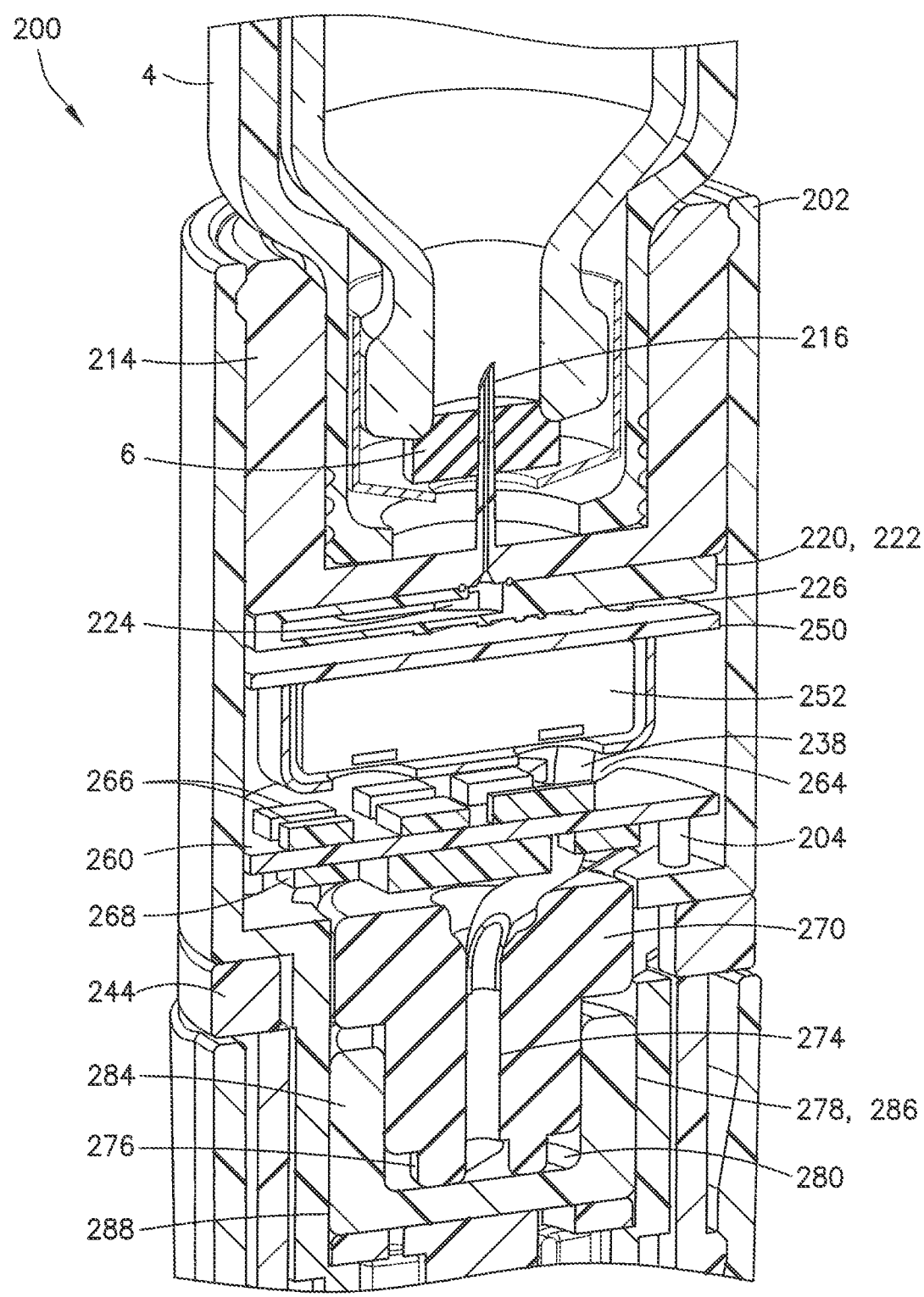
FIG. 3 illustrates a cross sectional view of the electronic exchange system.

According to one embodiment, FIG. 3 illustrates a cross sectional view of the electronic exchange system 200. The housing 202 encloses the components of the electronic exchange system 200. The housing 202, as illustrated in FIGS. 7 and 8, includes a plurality of printed circuit board (PCB) posts 204, slots 205 a recess 206 and a plurality of external ridges 208. Each of the plurality of PCB posts 204 is a boss extended from a bottom inner surface of the housing 202. The main board 260 is disposed on the top surface of each of the plurality of PCB posts 204. There are at least three PCB posts 204 disposed equidistant from each other and adjacent to an inner diameter of the housing 202.

The recess 206 is also disposed on the bottom inner surface of the housing 202. The recess 206 extends into the bottom inner surface to create a cavity for the upper septum 270 and the fluid conduit 238 to reside in. The recess 206 coupled with the plurality of PCB posts 204 provide a space so that the upper septum 270 and the fluid conduit 238 do not interfere with the main board 260 and its components 266. The plurality of external ridges 208 allows for proper operation of the needle assembly 100 as described in detail below.

The slots 205 are disposed along an outer surface of the housing 202 and adjacent to each side of the recess 206. As illustrated in FIG. 7, a portion of an outer circumference of the housing 202 adjacent to the recess 206 is indented to create the slots 205. The slots 205 are configured to engage a diffuser ring 244 as described below.

The hub 214 includes a hollow spike 216. As illustrated in FIG. 3, when the electronic exchange system 200 is mounted on the medication delivery pen 4 (non-patient end), a sharpened proximal end of the hollow spike 204 pierces a vial, cartridge or the reservoir septum 6 to establish fluid communication between the electronic exchange system 200 and the medication delivery pen 4. Specifically, the hollow spike 204 piercing the reservoir septum 6 provides fluid communication between the electronic exchange system 200 and an insulin cartridge, for example, of the medication delivery pen 4.

Figure 9:
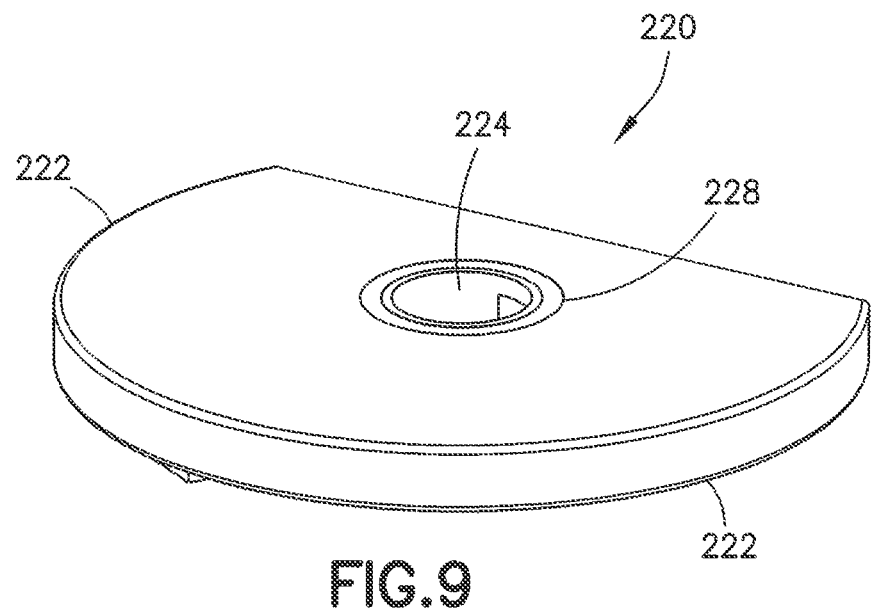
FIG. 9 illustrates a top perspective view of a flow sensor.
Figure 10:
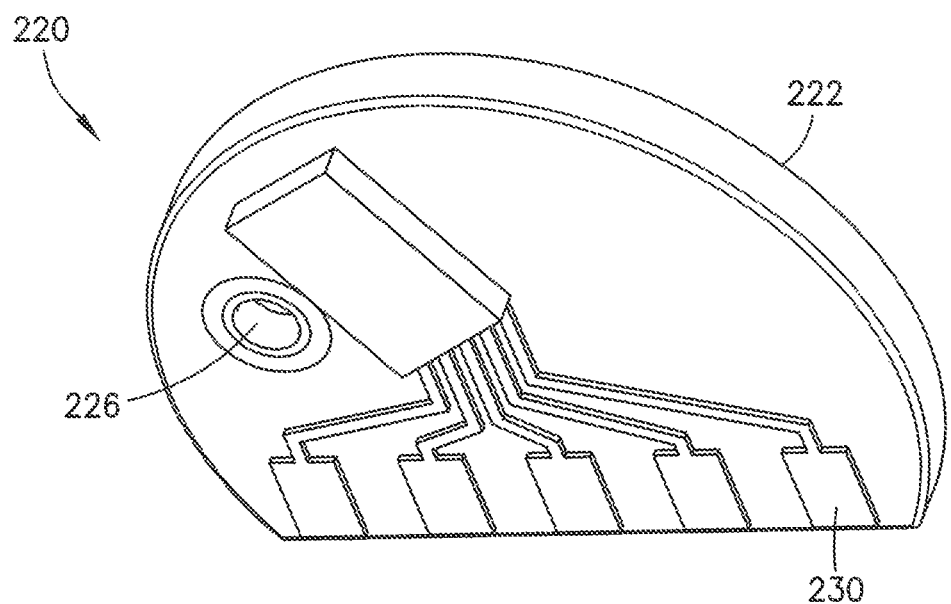
FIG. 10 illustrates a bottom perspective view of the flow sensor.

According to one embodiment, the electronic exchange system 200 further includes a flow sensor 220. The flow sensor 220, as illustrated in FIGS. 9-11, includes a flow sensor housing 222 that houses the electrical components of the flow sensor 220. Medicament travels through a fluid path 240 in the flow sensor 220 by entering via a sensor inlet 224 and exiting via a sensor outlet 226.

As illustrated in FIG. 3, the sensor inlet 224 is centered along a longitudinal edge of the flow sensor housing 222 and is aligned with the hollow spike 216 of the hub 214 in the electronic exchange system 200. The sensor inlet 224 includes a rubber seal or O-ring seal 228 that provides a hermetic or leak free interface between the flow sensor 220 and the hub 214. Such a configuration advantageously prevents medicament from contacting electrical components in the electronic exchange system 200. The sensor outlet 226 establishes a fluid connection to the fluid conduit 238 as described below.

The flow sensor 220 is advantageously configured so that there is no direct fluid contact between the medicament and a sensor chip or other electrical components. Instead, the fluid path 240 routes the medicament through the flow sensor housing 222 to measure and extract the necessary medicament flow data. Preferably, the flow sensor 220 is a Sensirion LPG10 flow sensor.

The flow sensor 220 further includes electrical contacts 230. The electrical contacts 230 are disposed on an external surface of the flow sensor housing 222 to communicate flow data. In the electronic exchange system 200, the battery hoard 250 is electrically connected to the flow sensor 220 to receive and analyze the flow data.

Figure 5:
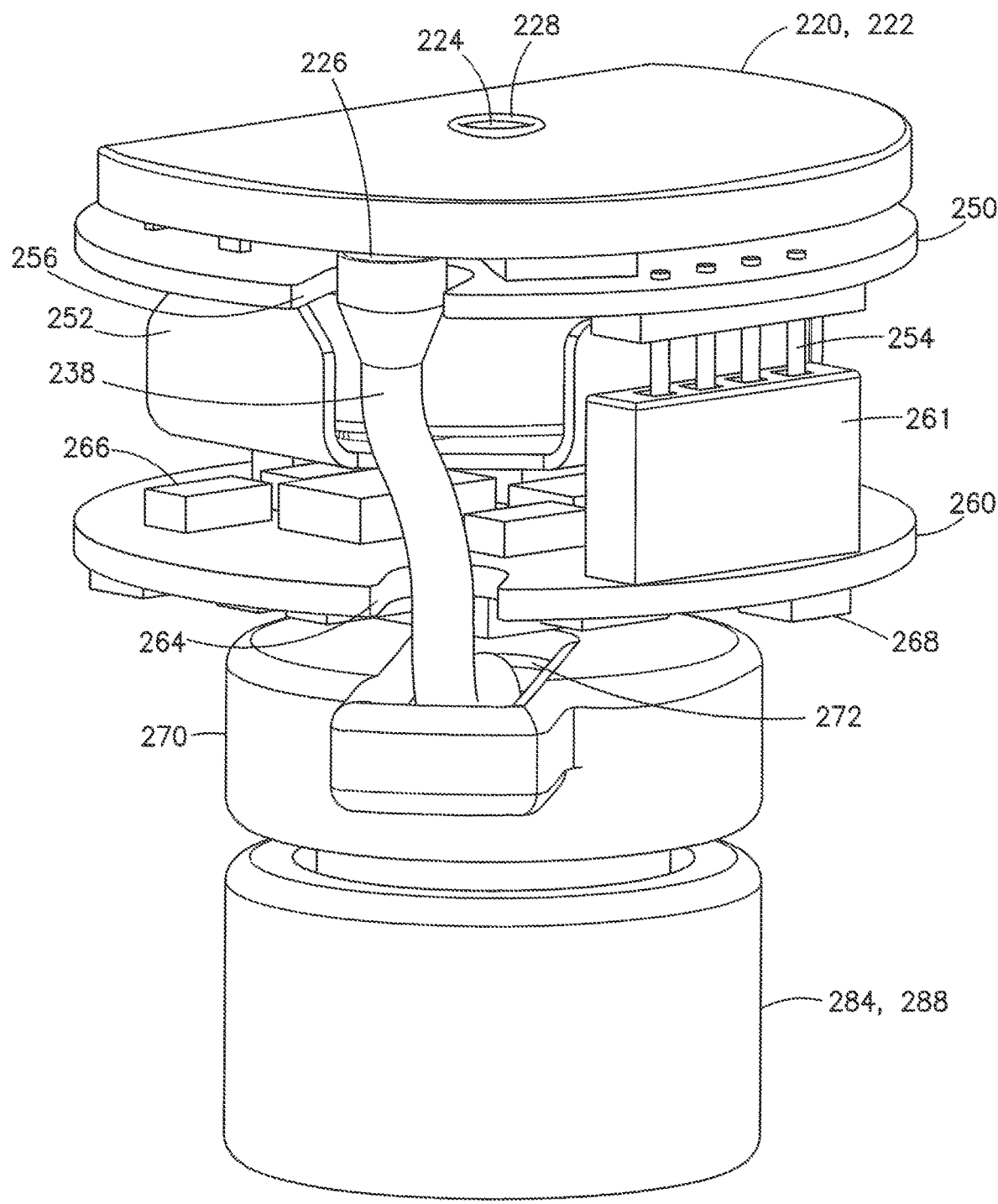
FIG. 5 illustrates a perspective view of a subassembly of the electronic exchange system.
Figure 6:
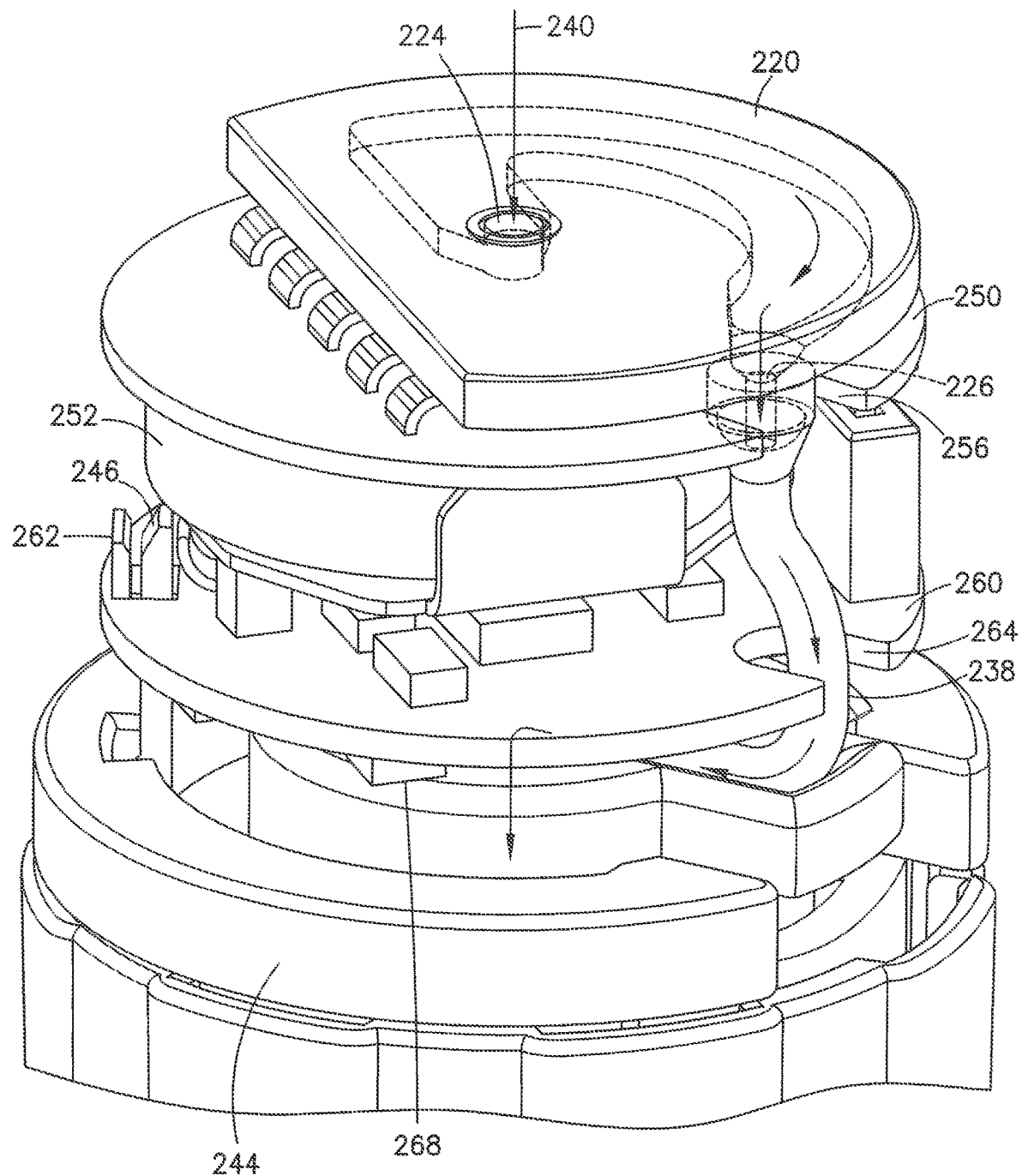
FIG. 6 illustrates a medicament flow path in a transparent perspective view of the electronic exchange system.
Figure 13:
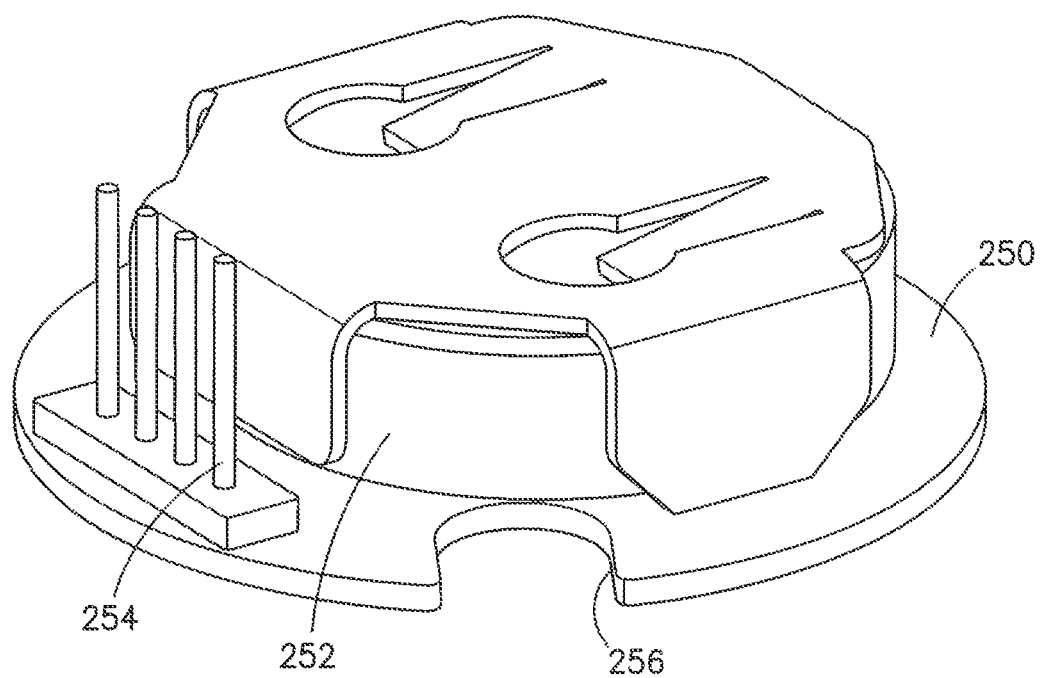
FIG. 13 illustrates a top perspective view of a battery board.

The electronic exchange system 200, according to one embodiment, also includes the battery board 250 (first board). The battery board 250, as illustrated in FIGS. 5, 6 and 13, is a printed circuit board electrically connected to a battery 252 and having battery contacts 254. The battery 252 provides power to operate the electronic exchange system 200. The battery 252 preferably includes a step-up converter to increase voltage. The battery board 250 also mechanically secures the battery 252.

Further, the battery board 250 is electrically connected to the flow sensor 220 to receive medicament flow data for analysis and to communicate this data to an external system such as a computer, smart phone or other electronic device. The battery board 250 also includes a first fluid path hole or opening 256. The first fluid path opening 236 is preferably a cutaway portion at a circumferential edge of the battery board 250. The first fluid path opening 256 provides a means to route the fluid path traveling in the fluid conduit 238. The first fluid path opening 256 is advantageously disposed along a circumferential edge of the battery board 250 to minimize interference between the fluid conduit 238 and the remaining electrical components of the electronic exchange system 200.

Beneath the battery board 250 in the electronic exchange system 200 according to one embodiment, is a main board 260 (second board). The main board 260, as illustrated in FIGS. 5, 6, 14 and 15, includes a battery board connector 261, snap on member 262, a second fluid path hole or opening 264, circuit board components 266 and a plurality of light emitting diodes (LEDs) 268.

The battery connector 261 electrically engages the battery contacts 254 on the battery board 250. The battery connector 261 provides electric power from the battery 252 to operate the main board 260. The snap on member 262 is a switch that activates the electronics on the main board 260. Further details of the diffuser ring 244 are described below.

The second fluid path hole or opening 264 is preferably a cutaway portion at a circumferential edge of the main board 260. Similar to the first fluid path opening 256, the second fluid path opening 264 provides a means to route the fluid path traveling in the fluid conduit 238. The second fluid path opening 264 is advantageously disposed along a circumferential edge of the battery board 250 and substantially aligned with the first fluid path opening 256 to minimize interference between the fluid conduit 238 and the remaining electrical components of the electronic exchange system 200.

Figure 14:
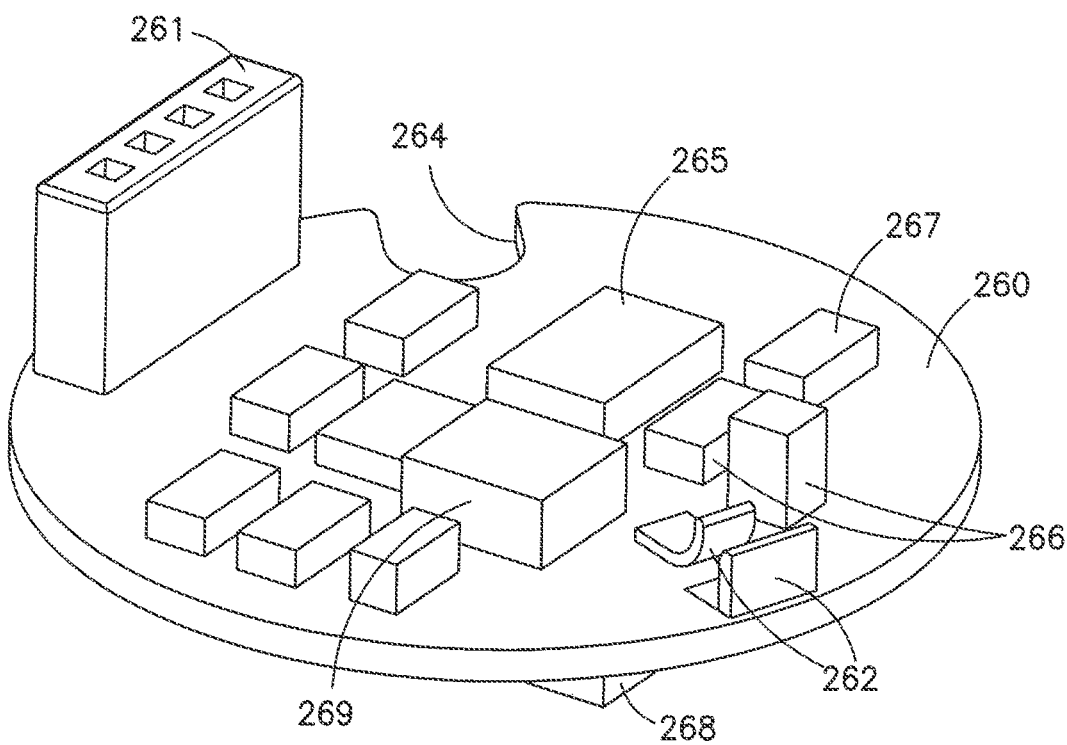
FIG. 14 illustrates a top perspective view of a main board.
Figure 15:
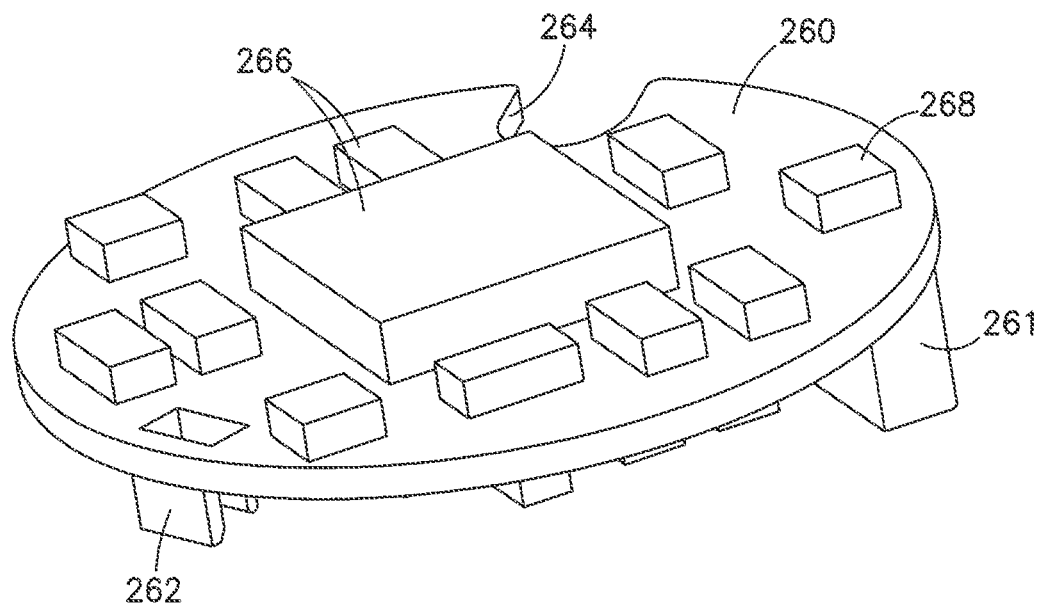
FIG. 15 illustrates a bottom perspective view of the main board of FIG. 14.

The main board 260, as illustrated in FIGS. 14 and 15, includes circuit board components 266 such as a plurality of LEDs 268, a Bluetooth chip 265 a memory chip 267 and a microprocessor 269. In an alternate configuration, a microprocessor and a memory chip included in a standard Bluetooth chip may be sufficient and not require these components separately on the main board 260. In this instance, the Bluetooth chip will require various simple circuit elements such as resistors, capacitors and diodes to function properly.

The plurality of LEDs 268, as illustrated in FIG. 15, preferably includes three LEDs and is spaced apart from each other in a circumferential direction and near an outer edge of the main board 260. The LEDs 268 are also disposed at a distal surface of the main board 260.

For example, if the LEDs 268 are together illuminating solid light, the electronic exchange system 200 is powered on and ready for operation. If the LEDs 268 are together blinking, the medicament is being delivered and will continue to blink for ten seconds after the dose is delivered to the patient. If the LEDs 268 are together not illuminated, the electronic exchange system 200 is powered off. Alternately, the LEDs 268 can illuminate in different colors or individually to indicate device status. For example, the LEDs 268 can illuminate different colors to indicate various error conditions (clogging or low battery, for example), as well as pairing status with a Bluetooth enabled external device.

The LEDs 268 also indicate when the electronic exchange system 200 is paired to the external system. Moreover, the LEDs 268 are illuminated during dosing to indicate flow status such as in "progress," "complete," "clogging," when the electrical communication is paired for real-time transfer of delivery data to the external system, and when the user can remove the delivery device needle (e.g., flow rate indicates injection is complete, or the microprocessor 269 determines the flow over a designated period of time matches an inputted dose amount), among other states.

As illustrated in FIG. 14, the Bluetooth chip 265 is also disposed on the main board 260. In the electronic exchange system 200, the Bluetooth chip 265 is disposed above and adjacent to the upper septum 270. The Bluetooth chip 265 provides data communication between the electronic exchange system 200 and the external system. Alternatively, Wi-Fi technology can be used in place of the Bluetooth chip 264 for similar purposes.

FIG. 14 further illustrates the memory chip 267 disposed on the main board 260. The memory chip 267 stores information when the flow data or any processed information is not transferred to the external system.

According to an alternate embodiment, data provided during or immediately after injection from the electronic exchange system 200 is automatically transferred and stored at a memory device in the external system with a time stamp using a dock in the external system. In this manner, the electronic exchange system 200 does not process the flow data. Instead, while dosing is in progress, the external system can be configured by an app, for example, to receive and process flow data to determine flow rate over time, total dose and other flow and dosing characteristics.

FIG. 14 also illustrates the microprocessor 269 disposed on the main board 260. The microprocessor 269 provides the following functional advantages and benefits. The microprocessor 269 receives a desired dose from the user via the Bluetooth chip 265 and analyzes the flow data received from the flow sensor 220 to determine a dose delivery completion status. The microprocessor 269 measures time through a global positioning system (GPS) or alternatively includes a real time clock (e.g., Abracon AB-RTCMC real-time clock module or equivalent thereof). The microprocessor 269 uses this time data to determine rate of delivery and time of delivery completion. When the dosing is being administered, the microprocessor 269 receives flow data from the flow sensor 220 and determines how much time is needed to deliver the desired dose, total dose delivered, dose time, dose rate, or dose status such as "in progress" or "complete." Additionally, flow data during delivery indicates issues such as clogging and generates user alerts during dosing. The microprocessor 269 also calculates a dose history for the user to access.

The microprocessor 269 transfers the data regarding drug delivery status (e.g., complete or in progress, as described above) or other delivery information (e.g., rate, timing, as described above) in real-time (e.g., during injection) or at any time such as after injection. For example, the electronic exchange system 200 captures time of dose and sends timing information with flow and total amount delivered data to the external system. This transfer occurs via the Wi-Fi technology or the Bluetooth chip 265 as described above.

Figure 16:
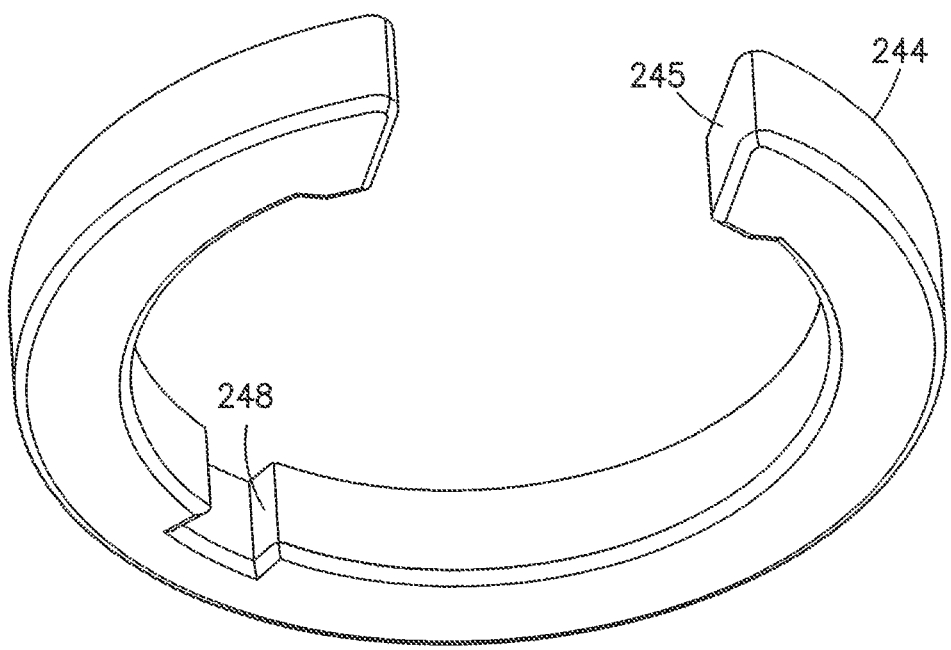
FIG. 16 illustrates a right perspective view of a diffuser ring.

According to one embodiment, as illustrated in FIG. 16, the electronic exchange system 200 includes the diffuser ring 244 having an opening 245 and a cut out portion 248. The diffuser ring 244, as illustrated in FIG. 3, is disposed below the main board 260 and is externally exposed. The diffuser ring 244 is retained between a top surface of an inner housing of the needle assembly 100 and a bottom surface of the housing 202. Specifically, as illustrated in FIGS. 2, 7 and 16, the opening 248 of the diffuser ring 244 snaps into the slots 205 located on the housing 202 to secure the diffuser ring 244.

Figure 22:
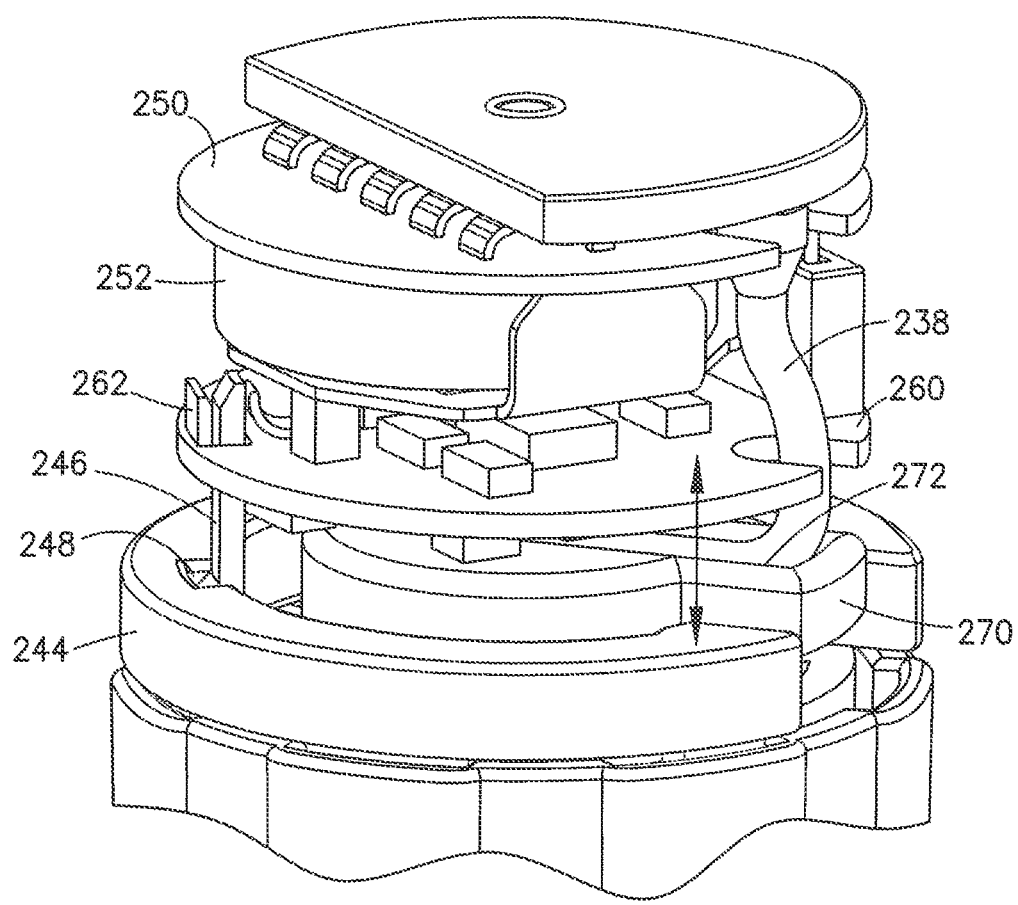
FIG. 22 illustrates a right perspective view of the diffuser ring secured to the main board.

As illustrated in FIG. 22, the cut out portion 248 of the diffuser ring 244 provides a passageway for a snap on flange 246. When a proximal end of the snap on flange 246 engages or activates the snap on member 262, the electronics on the main board 260 are activated. When the snap on flange 246 is disengaged from the snap on member 262, the electronics on the main board 260 are deactivated.

Figure 20:
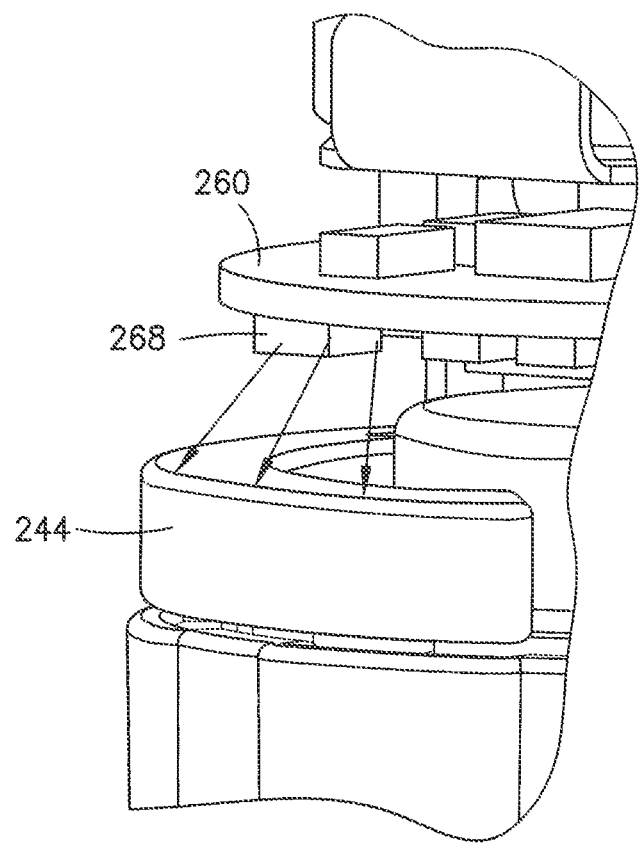
FIG. 20 illustrates a right perspective view of a light emitting diode (LED) interacting with the diffuser ring.
Figure 21:
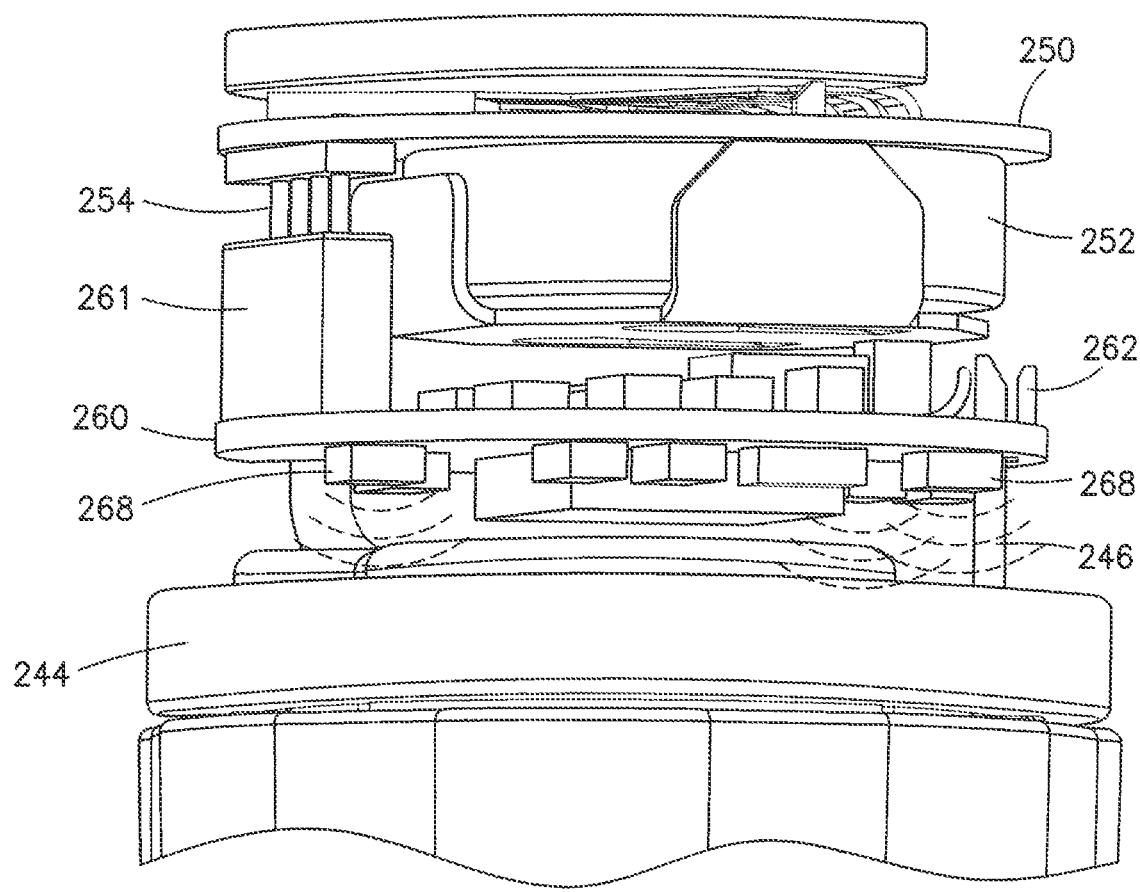
FIG. 21 illustrates a front perspective view of a plurality of LEDs interacting with the diffuser ring.

As illustrated in FIGS. 20 and 21, the diffuser ring 244 is translucent and configured to receive the light emitted from the LEDs 268 as described above. The diffuser ring 244 is configured to diffuse the light emitted by the LEDs 268 around an entire outer perimeter of the needle assembly 2 and the electronic exchange system 200. Preferably, the housing 202 is also partially transparent so that light from the LEDs 268 is not blocked from reaching the diffuser ring 244. In this manner, the device status of the electronic exchange system 200 is more obvious from various viewing angles. Also, the device status of the electronic exchange system 200 is determined by the user based on illumination of the diffuser ring 244.

The electronic exchange system 200, according to one embodiment, further includes the fluid conduit 238 having an inlet 247 and an outlet 249. FIG. 12 illustrates the fluid conduit 238 and its general contour. FIGS. 5 and 6 illustrate that the inlet 247 of the fluid conduit 238 is connected to the sensor outlet 226 of the flow sensor 220. Subsequently, the fluid conduit 238 travels through the battery board 250 and the main board 260 via the first and second fluid path openings 256, 264. Ultimately, the outlet 249 of the fluid conduit 238 is connected to the upper septum 270.

FIG. 6 illustrates the medicament fluid path 240 when entering through the spike 216 of the hub 214, traveling through the flow sensor 220 and moving into the fluid conduit 238, and exiting to the upper septum 270. Once the medicament enters the upper septum 270, the medicament is ready to be transmitted to the needle assembly 100 for medication delivery.

Figure 18:
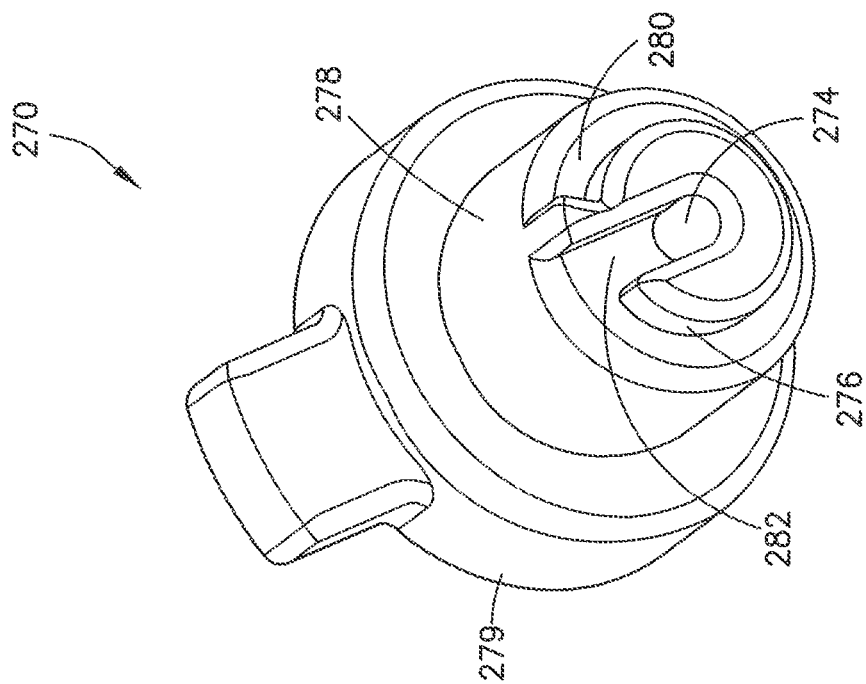
FIG. 18 illustrates a bottom perspective view of the upper septum.
Figure 17:
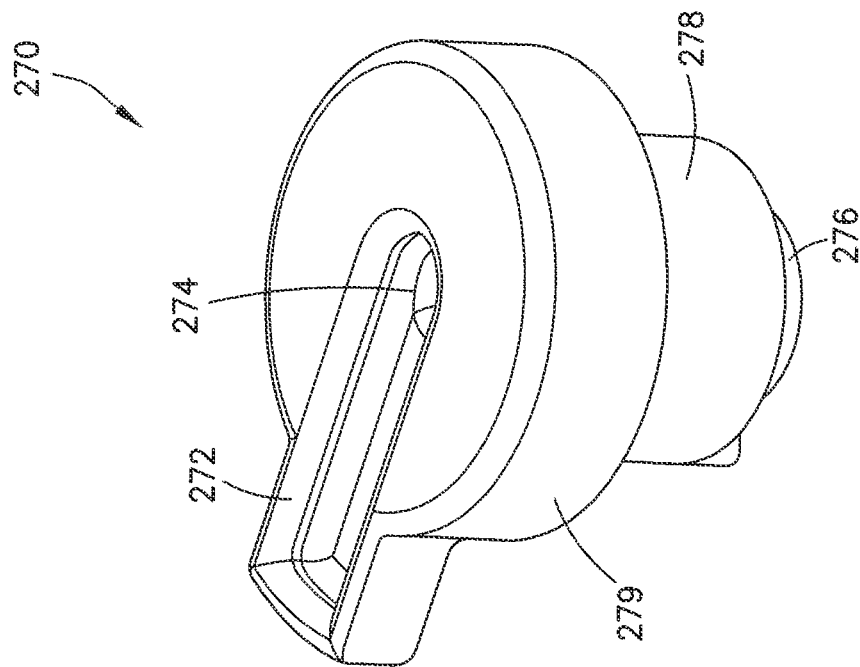
FIG. 17 illustrates a top perspective view of an upper septum.

According to one embodiment, the electronic exchange system 200 further includes the upper septum 270 and the lower septum 284 (generally referred to as septum body 270/284). FIGS. 17 and 18 illustrate the upper septum 270 including a recess 272 and having a through hole or input chamber 274 at its center. Specifically, the recess 272 is a cavity that recedes into a proximal surface of the upper septum 270. As illustrated in FIG. 3, the recess 272 provides a space for the fluid conduit 238 to be disposed. Moreover, the recess 272 extends beyond an outer diameter (third diameter) 279 of the upper septum 270 and acts like an alignment key for proper orientation when engaging the recess 206 in the housing 202.

At the center of the upper septum 270 is the input chamber 274. As illustrated in FIG. 3, the input chamber 274 extends through the upper septum 270 and provides a passageway for medicament to exit the outlet 249 of the fluid conduit 238 and enter into the upper septum 270. A distal end of the input chamber 274 is in fluid communication with a delivery chamber 280. The input chamber 274 allows liquid medicament to flow from a medication delivery pen into the delivery chamber 280.

The delivery chamber 280 is formed when the upper and lower septums 270, 284 are joined together. Specifically, in addition to the outer diameter (third diameter) 279, the upper septum 270 includes a first diameter 276 and a second diameter 278. The third diameter 279 is the largest diameter while the first diameter 276 is the smallest diameter. The second diameter 278 seals the upper septum 270 to the lower septum 284.

As illustrated in FIG. 3, the outer surface of the first diameter 276 and a bottom distal surface of the second diameter 278 form the delivery chamber 280. In other words, the delivery chamber 280 is disposed between outer surfaces of the first and second diameters 276, 278 of the upper septum 270. The delivery chamber 280 is a circular cavity that is in fluid communication with a longitudinal cavity 282 of the upper septum 270. The longitudinal cavity 282 is a passageway that connects the delivery chamber 280 (circular cavity) to the input chamber 274. The longitudinal cavity 282 extends from the first diameter 276 to the center of the upper chamber 270 along a bottom distal surface of the second diameter 278.

Figure 19:
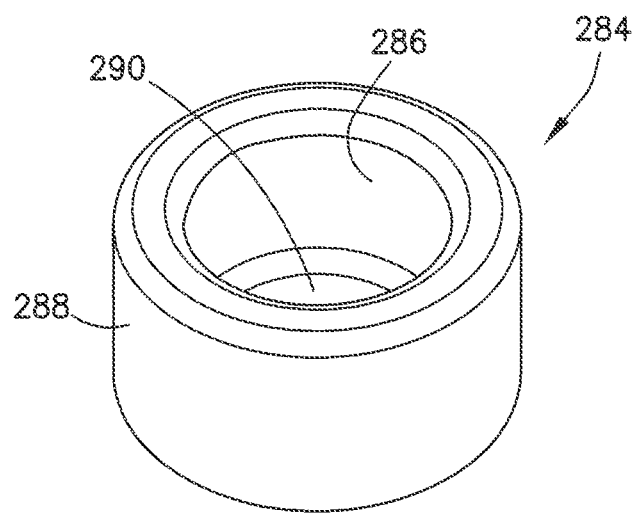
FIG. 19 illustrates a top perspective view of a lower septum.

The lower septum 284 or priming septum is illustrated in FIG. 19. The lower septum 284 includes an inner diameter 286, an outer diameter 288 and a bottom inner surface 290. The inner diameter 286 mates with the second diameter 278 of the upper septum 270 and provides direct sealing contact. The delivery chamber 280 is thus formed within the inner diameter 286 and above the bottom inner surface 290 of the lower septum 284, as well as outside the first diameter 276 and below the second diameter 278 of the upper septum 270. The delivery chamber 280 stores the medicament received from the input chamber 274 for medication delivery via an exemplary needle assembly.

The upper septum 270 is secured to the lower septum 284 via an annular snap fit or an interference fit, for example. The upper septum 270 and the lower septum 284 are preferably composed of different materials having different durometers. Such characteristics enhance sealing between the second diameter 278 of the upper septum 270 and the inner diameter 286 of the lower septum 284.

Figure 23:
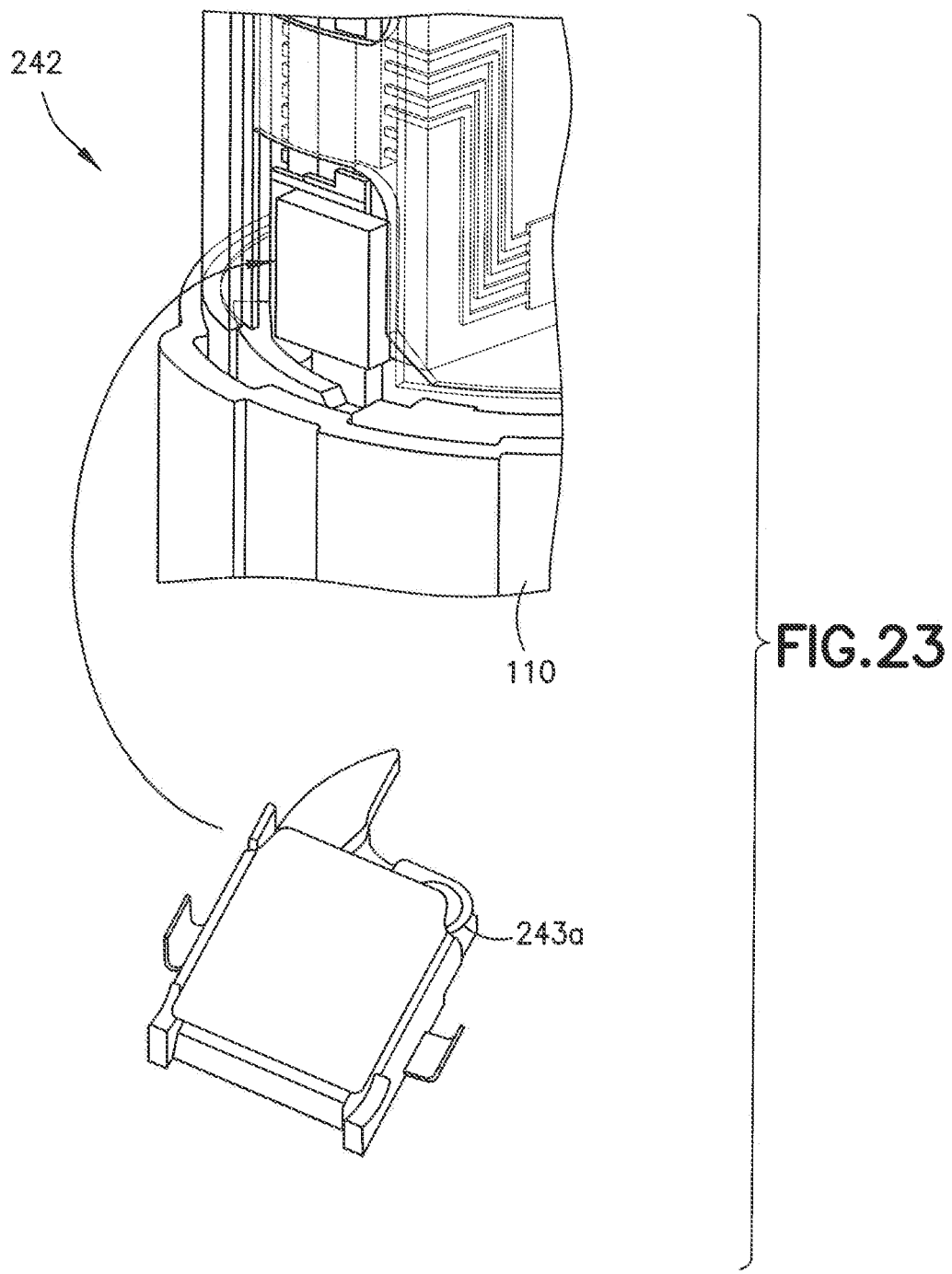
FIG. 23 illustrates an electronic exchange system including an activation switch being a detector switch.
Figure 24:
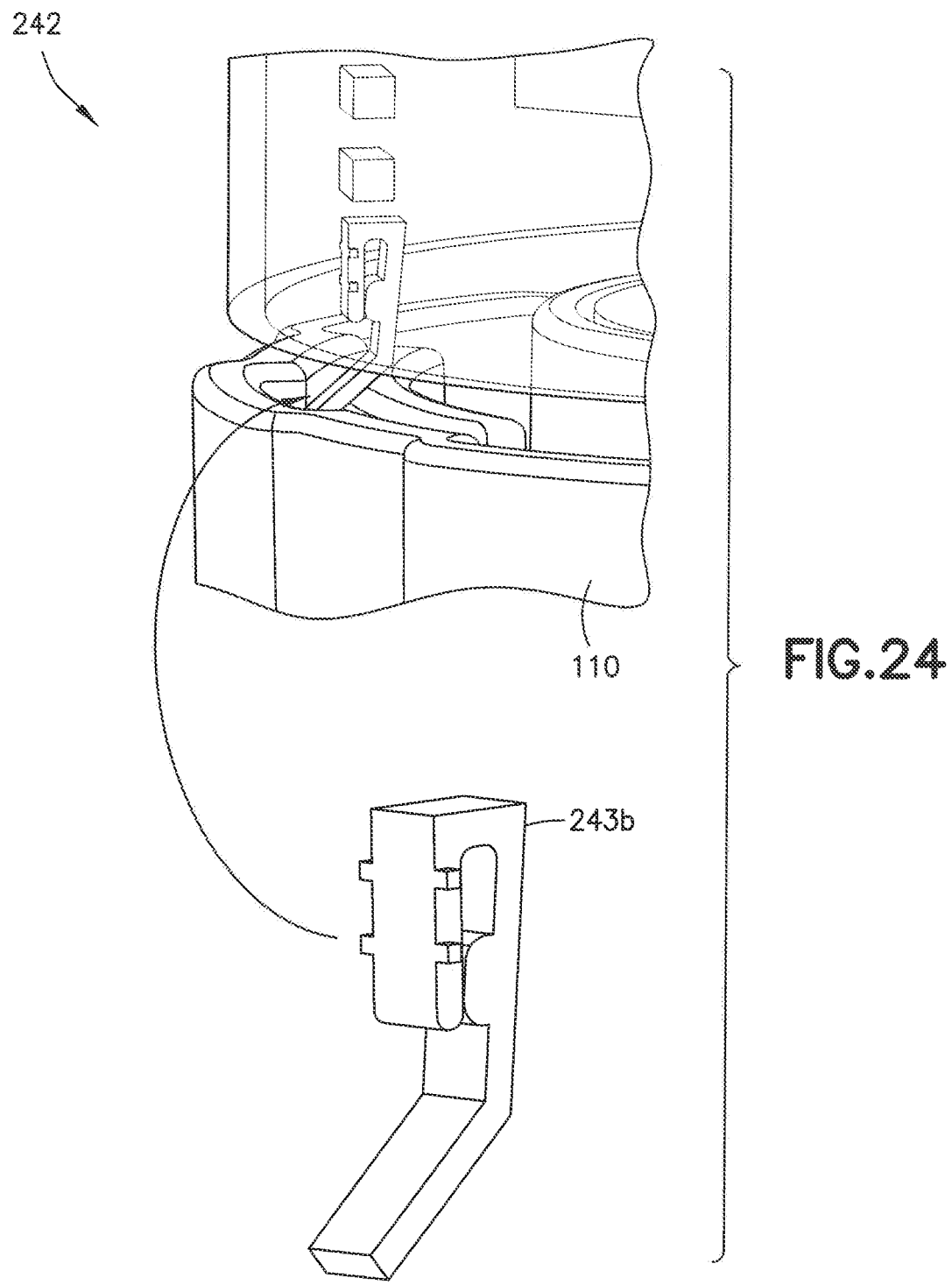
FIG. 24 illustrates an electronic exchange system including an activation switch being a tactile switch.

The electronic exchange system 200, according to one embodiment, can provide alternate means for activation. FIGS. 23-25 illustrate various activation switches 242. Each of the activation switches 242 are initiated when the user moves a housing 110 of a needle assembly 100, as described further below. When the activation switch 242 is turned on, the LEDs 268 are illuminated in a similar manner as described above to show readiness of the electronic exchange system 200.

FIG. 23 illustrates the activation switch 242 being a detector switch 243a. The detector switch 243a will detect and determine when the housing 110 covers a predetermined portion of the electronic exchange system 200 to activate the electronic exchange system 200. FIG. 24 illustrates the activation switch 242 being a flanged switch 243b. When the housing 110 moves and covers a predetermined portion of the electronic exchange system 200, the flanged switch 243h deflects and thus activates the electronic exchange system 200. FIG. 25 illustrates the activation switch 242 being a Hall Effect sensor 243c. The Hall Effect sensor 243c includes a magnet and a Hall Effect switch. The magnet is disposed in the housing 110 and a Hall Effect switch is disposed on an exterior surface of the electronic exchange system 200. When the housing 110 moves and aligns the magnet to the Hall Effect switch, the Hall Effect sensor 243c activates the electronic exchange system 200.

Figure 25B:
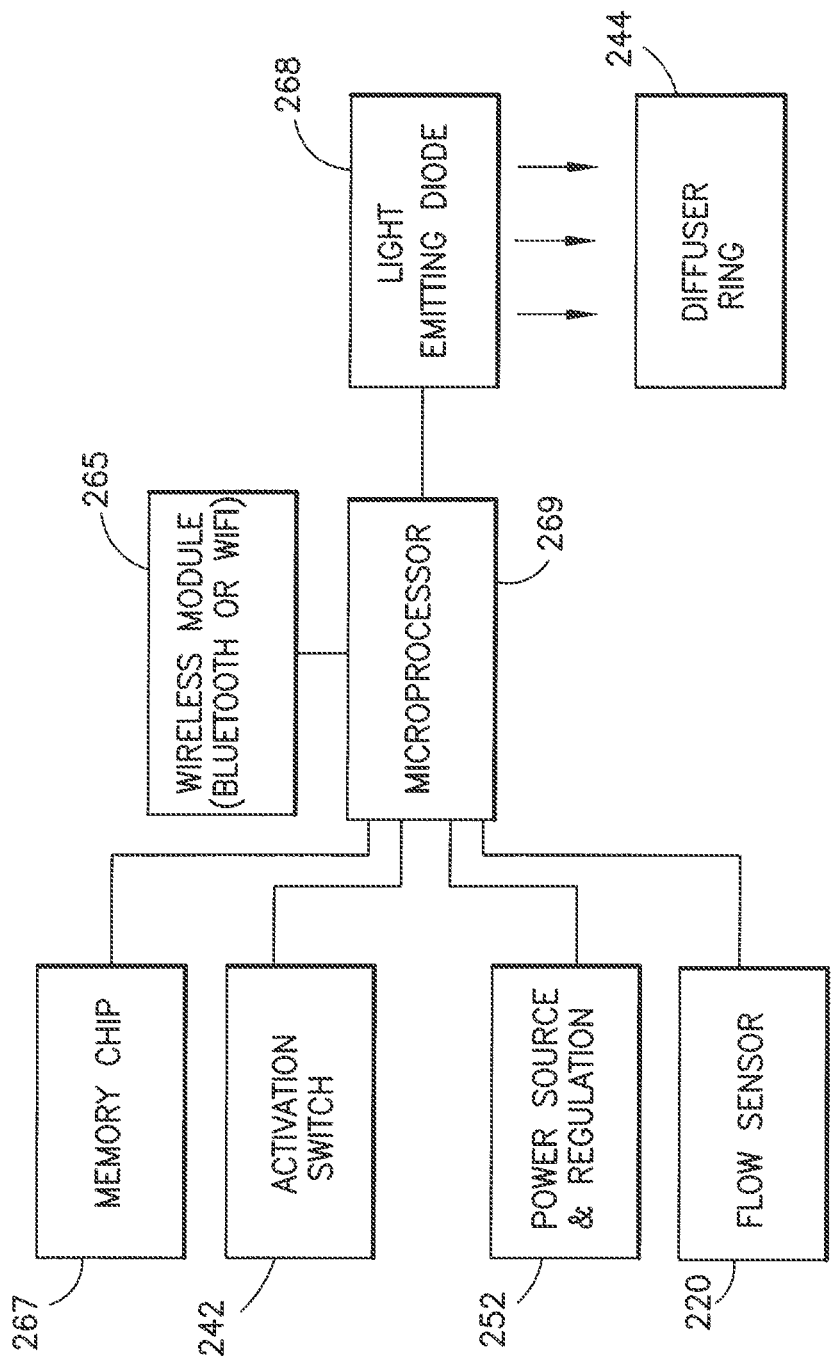
FIG. 25B illustrates a block diagram of the operation of the circuit board in the electronic exchange system.

FIG. 25B illustrates a block diagram showing the operation of the circuit hoard 250, 260 in the magazine electronic exchange system 200. Specifically, the memory chip 267, the activation switch 242, the power source and regulation (i.e. the battery) 252 and the flow sensor 220 cooperate with the microprocessor 269 for appropriate operation as described above. The microprocessor 269 also communicates with the wireless module (i.e. Bluetooth chip) 265 and the light emitting diode 268 to illuminate the diffuser ring 244 for efficient power usage and transfer of data.

Figure 4A:
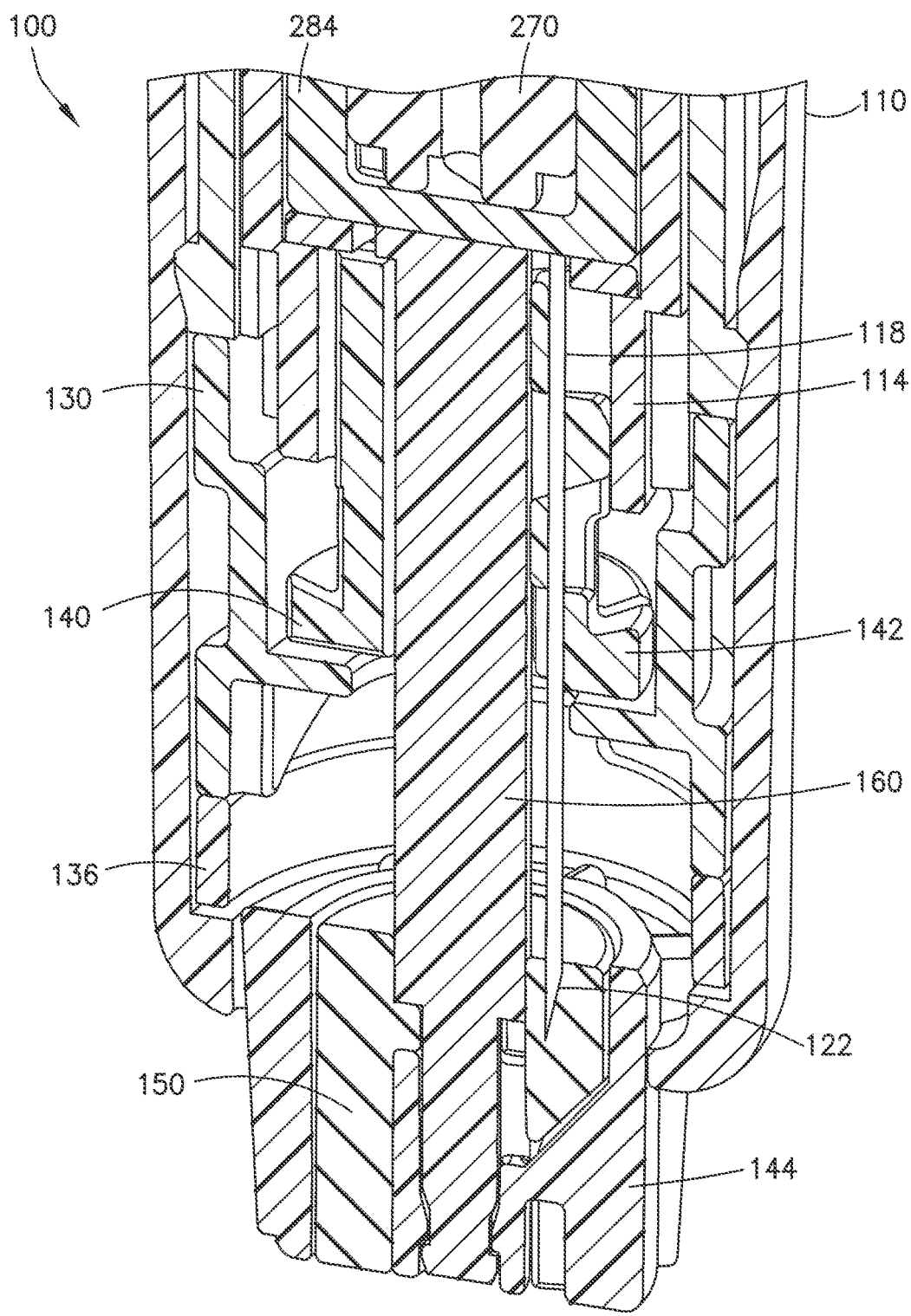
FIG. 4A illustrates a cross sectional view of the needle assembly connected to the electronic exchange system in a first position.
Figure 4B:
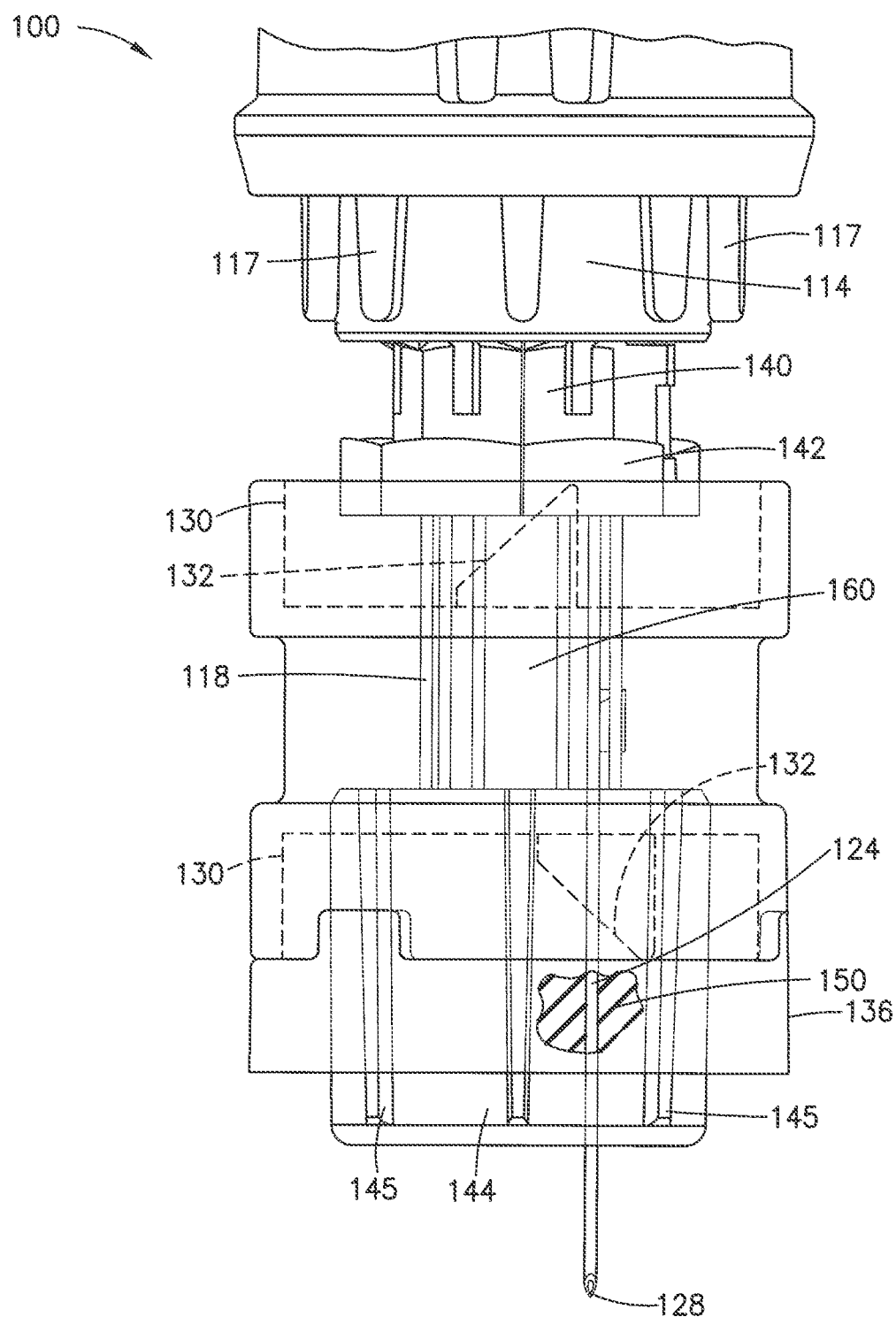
FIG. 4B illustrates a cross sectional view of the needle assembly connected to the electronic exchange system in a second position.

FIGS. 4A and 4B illustrate the electronic exchange system 200 cooperating with a needle assembly 100. The following describes the operation of the needle assembly 100. According to one embodiment, the needle assembly 100 moves from a first position, as illustrated in FIG. 4A, and toward a second position, as illustrated in FIG. 4B, where a distal end 128 of a selected needle 124 of the plurality of needles 118 is exposed for medicament delivery. As the needle assembly 100 leaves the first position, the distal end 128 of the selected needle 124 begins to pierce a sealing septum 150 and the remaining plurality of needles 118 are all sealed and sterilized in the sealing septum 150.

When the housing 110 moves downward, a follower ring 130 and a snap ring 136 move downward as well. As the follower ring 130 moves downward, a follower 132 at a bottom portion of the follower ring 130 engages one of a plurality of external fins 145 of a bottom guide 144. Specifically, the follower 132 contacts one of the plurality of external fins 145 and the follower 132 slides along its tooth shaped edge to rotate the follower ring 130 while maintaining contact with the external fin 145.

A snap ring 136 also rotates because the snap ring 136 is rotationally connected to the follower ring 130. Since the snap ring 136 is rotationally coupled to the follower ring 130, the snap ring 136 applies pressure to an extending portion 142 of a needle post 140 of the selected needle 124. As a result, FIG. 4B illustrates the distal end 128 of the selected needle 124 piercing the sealing septum 150 of the needle assembly 100 and exposing the selected needle 124 for medication delivery.

When the needle assembly 100 is in the second position, as illustrated in FIG. 4B, the selected needle 124 of the plurality of needles 118 is exposed for medicament delivery. Specifically, the follower 132 has completed rotation and is disposed between external fins 145 of the bottom guide 144. The distal end 128 of the selected needle 124 is ready for medication delivery. In this second position, a proximal end of the selected needle 124 enters into fluid communication with the delivery chamber 280 and the sharpened distal end 128 of the selected needle 124 pierces the sealing septum 150 and is exposed. Each of the plurality of needles 118 is aligned and configured to be in fluid communication with the delivery chamber 280 when selected by the snap ring 136. The proximal end 120 of the remaining needles 118 continues to be disposed in the upper septum 270. The distal end 122 of the remaining needles 118 also continues to stay sealed and sterilized in the sealing septum 150 of the needle assembly 100.

When the needle assembly 100 returns from the second position back to the first position as illustrated in FIG. 4A, the user pulls the housing 110 back toward the medication delivery pen 4. At the same time, a cap pushes the snap ring 136 and the follower ring 130 upwards which moves the extending portion 142 of the selected needle 124 upward. The distal end 128 of the selected needle 124 returns into the sealing septum 150 of the needle assembly 100. The sealing septum 150 encloses the selected needle 124 and protects the user.

Meanwhile, the follower 132 at the top portion of the follower ring 130 contacts one of a plurality of ridges 117 of a septum housing 114 and causes the follower ring 130 to rotate. The plurality of ridges 117 can be disposed externally or internally to the septum housing 114. The follower 132 at the top portion of the follower ring 130 contacts one of the plurality of external ridges 117 of the septum housing 114 and the follower 132 slides along its tooth shaped edge to rotate the follower ring 130 while maintaining contact with the external ridge 117.

As the needle assembly 100 returns to the first position, as illustrated in FIG. 4A, the follower ring 130 rotates and prepares the snap ring 136 to align with an adjacent needle of the plurality of needles 118 for a subsequent injection. Specifically, the snap ring 136 elastically deflects in a radial direction and snap over the extending portion 142 of the needle post 140 of the adjacent needle of the plurality of needles 118. In this manner, the next needle in the needle assembly 100 is ready for subsequent use.

The process of moving from the first position to the second position and back to the first position while rotating the snap ring 136 repeats in the manner describe above so that each needle amongst the plurality of needles 118 of the needle assembly 100 is individually exposed in a consecutive manner from a first needle, to each adjacent needle and to a last needle.

Figure 26:
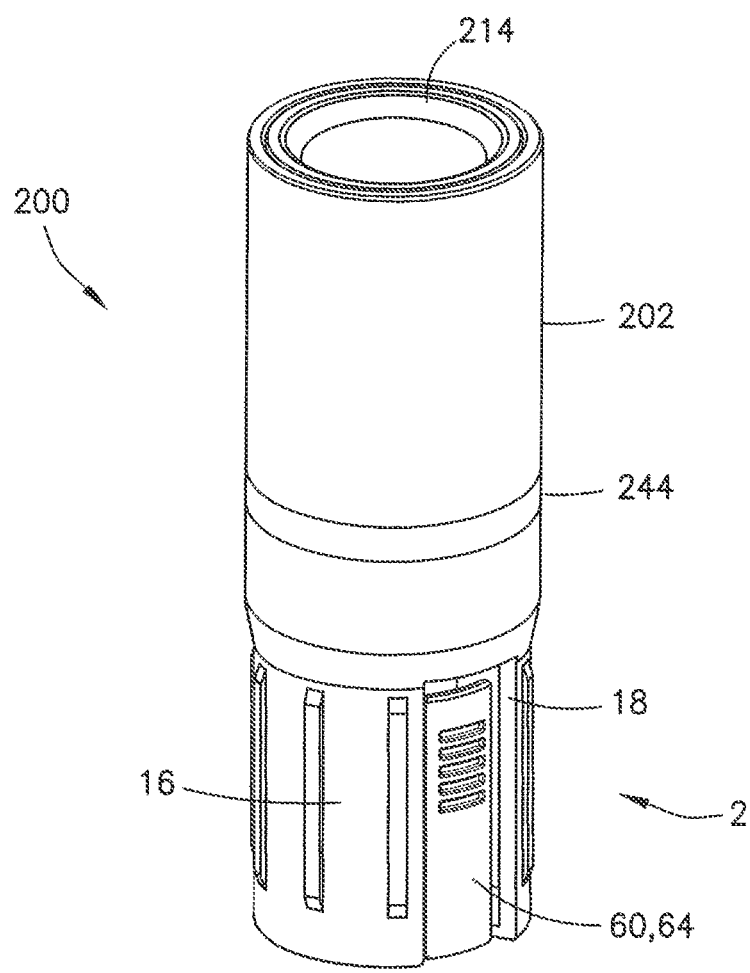
FIG. 26 illustrates a front perspective view of an electronic exchange system connected to another embodiment of the needle assembly.
Figure 27:
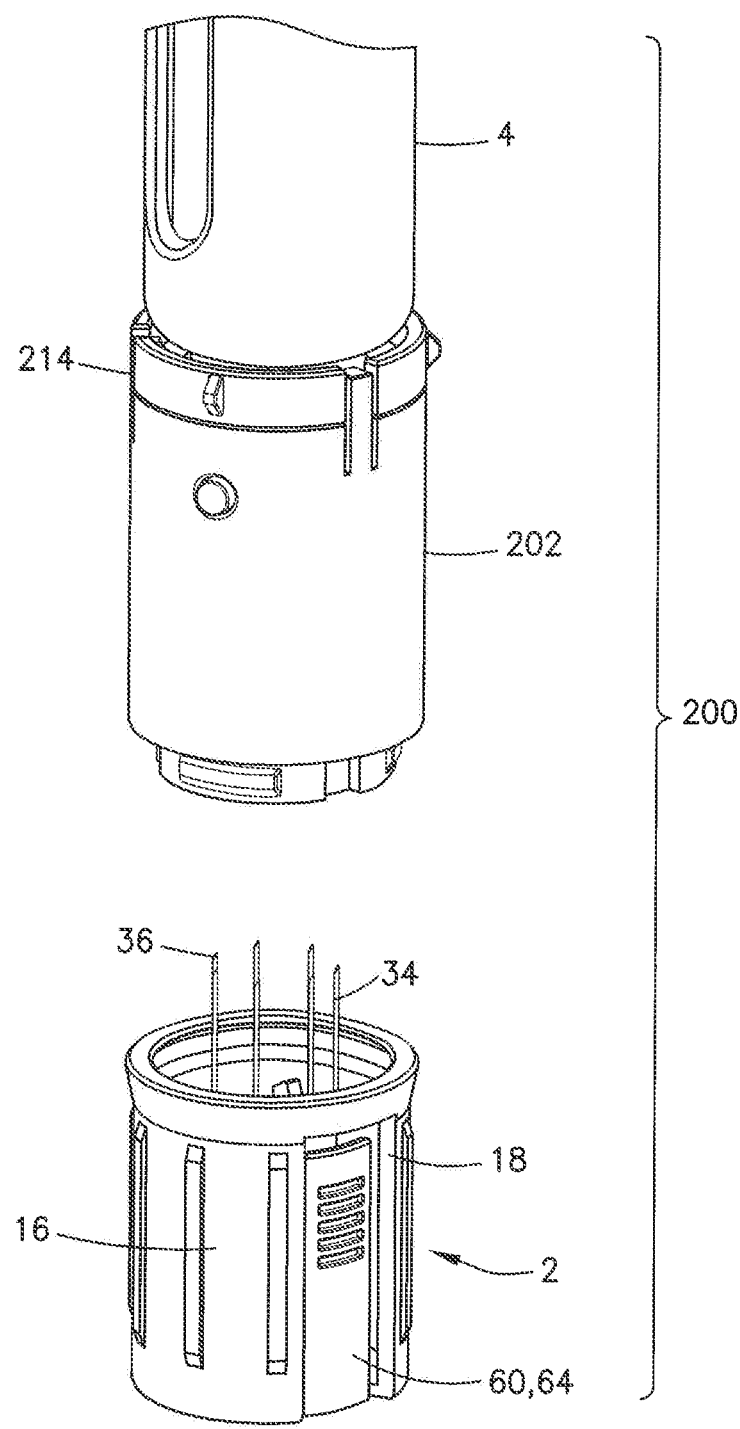
FIG. 27 illustrates a front perspective view of an electronic exchange system connected to a medication delivery pen and attachable to the needle assembly of FIG. 26.

FIGS. 26-30, according to one embodiment, illustrate another exemplary needle assembly 2 that connects to the electronic exchange system 200. FIG. 27 illustrates a typical medication delivery pen 4 used for injecting medicament, such as liquid drugs, into a living body. The electronic exchange system 200 is mounted on the medication delivery pen 4 to analyze medicament flow. The needle assembly 2 is configured to mount on the electronic exchange system 200 to enhance medication delivery by providing a plurality of needles 34 with sharp proximal ends 36 for use. After the needle assembly 2 is used, another needle assembly 2 can be used so that the medication delivery pen 4 and the electronic exchange system 200 can continue to operate as needed.

Figure 28:
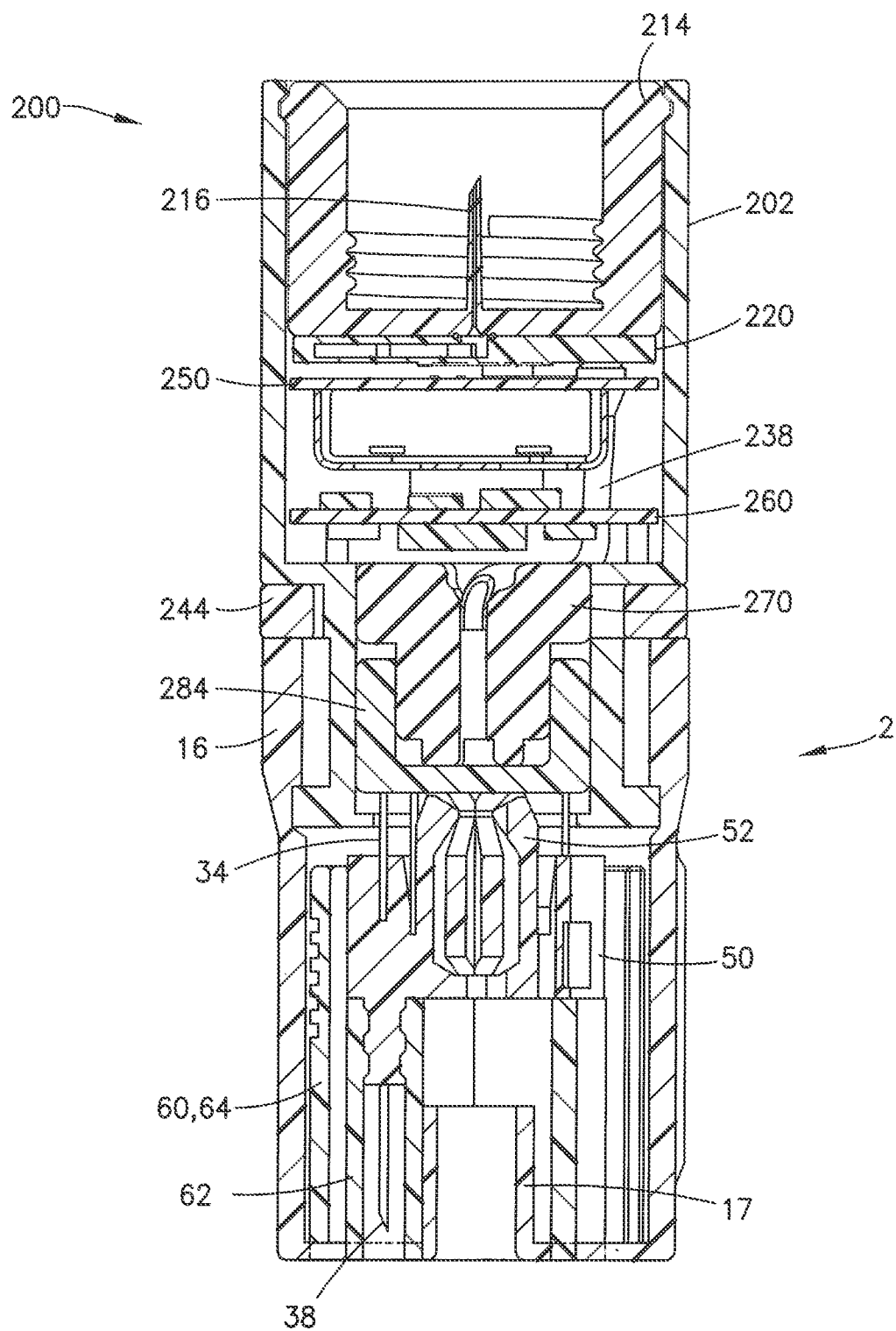
FIG. 28 illustrates a cross sectional view of an electronic exchange system connected to the needle assembly of FIG. 26 in a first position.

The sharpened proximal end 36 of the plurality of hollow needles 34 is disposed in the upper septum 270 in a first position of the needle assembly 2 as illustrated in FIG. 28. The plurality of needles 34 extends through the delivery chamber 280, thus contacting the medicament. However, the plurality of needles 34 is not in fluid communication with the delivery chamber 280.

Figure 29:
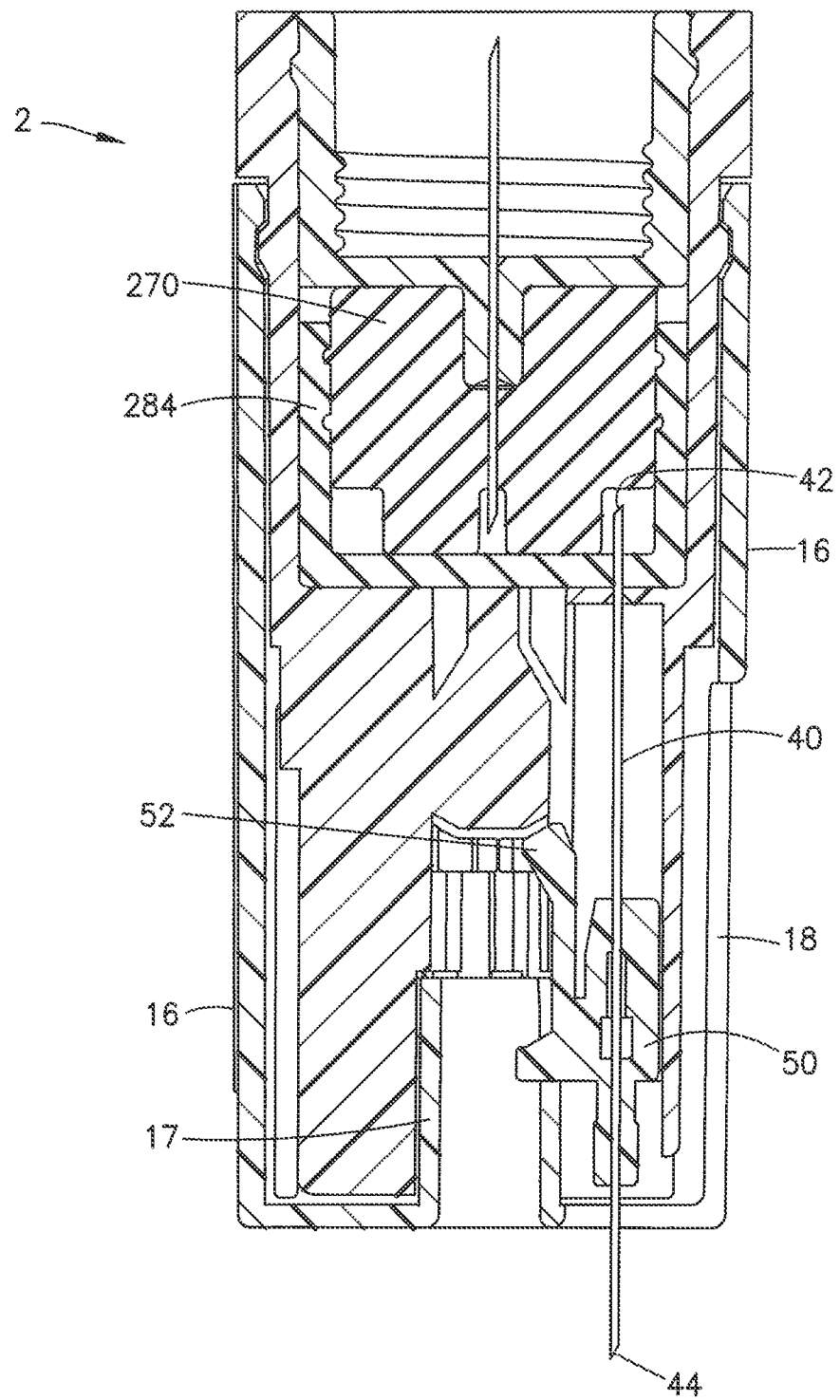
FIG. 29 illustrates a cross sectional view of an electronic exchange system connected to the needle assembly of FIG. 26 in a second position.

In a second position of the needle assembly 2, as illustrated in FIG. 29, one of the plurality of needles 34 is exposed for medicament delivery. In this instance, a proximal end 42 of a selected needle 40 is disposed in the circular cavity 280 to receive medicament.

The operation of the needle assembly 2 connected to the electronic exchange system 200 is now explained in an exemplary manner as follows. According to one embodiment, as illustrated in FIG. 26, the user connects the needle assembly 2 to the electronic exchange system 200. FIGS. 27 and 28 illustrate that when the user desires to use the needle assembly 2 for medication delivery, the selector ring 16 is rotated to align with a peel tab 60. The user bends the tab 64 of the peel tab 60 of the selected needle 40 from a retracted, compact position to an extended position.

Next, the user pulls the tab 64 of the peel tab 60 of the selected needle 40 and moves the needle assembly 2 from the first position of FIG. 28 to the second position of FIG. 29. When the selected needle 40 is fully drawn out, the needle assembly 2 is in the second position. Subsequently, the sterility barrier 60 is removed from the selected needle 40 and the needle assembly 2 is ready for medicament delivery. When the needle assembly 2 moves from the first position to the second position, the needle post 50 of the selected needle 40 also moves from a top position to a bottom position.

In the second position of the needle assembly 2, a proximal end 42 of the selected needle 40 also enters into fluid communication with the delivery chamber 280 of the electronic exchange system 200. A distal end 44 of the selected needle 40 exits the selector ring 16 and is exposed for medication delivery. Accordingly, medicament is received by the proximal end 42 of the selected needle 40 and exits the distal end 44 of the selected needle 40 to be delivered to a patient.

When the first needle of the plurality of needles 34 is used, the delivery chamber 280 is filled with medicament, resulting in the needle assembly septum being primed. Specifically, medicament must traverse and fill the complete fluid path of the delivery chamber 280 to reach the first needle of the plurality of needles 34. Accordingly, the incidence of air in the delivery chamber 280 is advantageously reduced. Removing air from the fluid path also advantageously improves dose accuracy.

Figure 30:
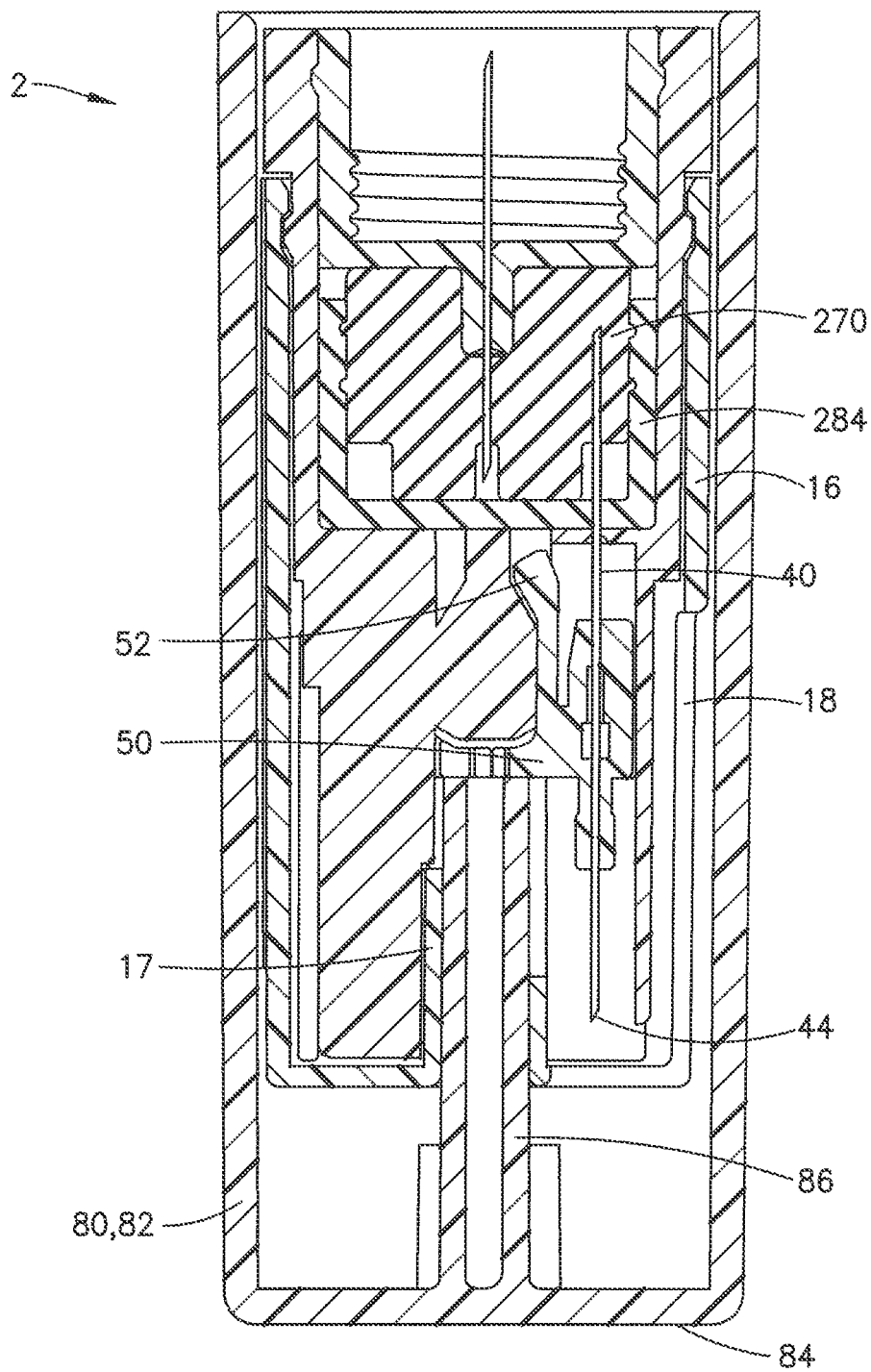
FIG. 30 illustrates a cross sectional view of the needle assembly connected to the electronic exchange system of FIG. 26 assembled with a cover in the first position.

FIG. 30, according to one embodiment, illustrate the use of the cover 80 to return the needle assembly 2 from the second position to the first position. The cover 80 includes a cylinder 82, a base 84 and a protrusion 86. The cylinder 82 is configured to surround the needle assembly 2. The base 84 is configured to cover a bottom portion of the selector ring 16 of the needle assembly 2. The protrusion 86 extends from the base 84 and is disposed centrally within the cylinder 82. When the cover 80 is placed on the needle assembly 2, the protrusion 86 enters a selector hole 17 of the selector ring 16. The protrusion 86 of the cover 80 applies pressure by pushing the needle post flange 52 of the needle post 50 of the selected needle 40 from the bottom position to the top position.

The protrusion 86 of the cover 80 moves the needle post 50 by applying pressure to the needle post flange 52. FIG. 30 illustrates the first position of the needle assembly 2. The needle post flanges 52 of each of the plurality of needles 34 are also illustrated to be arranged toward a central axis of the selector ring 16. Such a configuration advantageously allows the protrusion 86 of the cover 80 to engage each of the plurality of needle posts flanges 52 to move the needle post 50 from the bottom position to the top position.

After the needle assembly 2 is returned to the first position, according to one embodiment, an adjacent needle is preferably selected for use. The selector ring 16 is then rotated to expose an adjacent peel tab 60 of the adjacent needle. However, the user has the flexibility to expose and choose any of the remaining plurality of peel tabs 60.

Once a needle and respective peel tab 60 is selected, the selected peel tab 60 is removed for operation in the manner described above. The selected needle 40 is then used for medication delivery and afterwards, the cover 80 is used to return the selected needle 40 to the first position of the needle assembly 2. These steps are repeated until all of the plurality of needles 34 is used. The combination of the selector ring 16 and the plurality of peel tabs 60 simplify the needle assembly 2, allow for easy to use operation and improve safety.

Each of the plurality of needles 34 is advantageously isolated from the septum of the medication delivery pen 4 throughout the operation of the electronic exchange system 200 and the needle assembly 2. Also, the needle assemblies 2, 100 can include a USB port to transfer data. Such an arrangement advantageously provides simplicity in design, improves sterility, allows data transfer and provides a separation between a patient end and a non-patient end.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An electronic system connectable to a medication delivery pen and to a needle assembly, the electronic system exchanging data regarding a medicament traveling from the medication delivery pen to the needle assembly, the electronic system comprising:
   a hub having a spike that is configured to engage the medication delivery pen and configured to pierce a reservoir septum of the medication delivery pen;
   a flow sensor that is in fluid communication with the hub to measure flow data of the medicament;
   one or more circuit boards electrically contacting the flow sensor to process and transmit the flow data, the one or more circuit boards include one or more fluid path openings to route a flow of the medicament; and
   a septum body that is configured to provide fluid communication between the flow sensor and one of a plurality of needles of the needle assembly to administer the medicament to a patient; wherein
   the flow of the medicament does not contact the one or more circuit boards.

2. The electronic system of claim 1, wherein the one or more circuit boards includes a first circuit board and a second circuit board that are electrically connected to each other.

3. The electronic system of claim 2, wherein the first circuit board is electrically connected to a battery and the second circuit board is electrically connected to one or more LEDs.

4. The electronic system of claim 2, wherein the first circuit board is electrically connected to the flow sensor.

5. The electronic system of claim 1, further comprising a fluid conduit that transfers the medicament from the flow sensor to the septum body.

6. The electronic system of claim 5, wherein the fluid conduit is disposed in the one or more fluid path openings of the one or more circuit boards.

7. The electronic system of claim 5, wherein the fluid conduit routes the flow of medicament around the one or more circuit boards.

8. The electronic system of claim 1, wherein
the one or more circuit boards includes one or more LEDs to indicate device status; and
the one or more LEDs are disposed at a distal end of the one or more circuit boards.

9. The electronic system of claim 1, further comprising an activation switch comprising a Hall effect sensor that activates the electronic system.

10. The electronic system of claim 1, further comprising an activation switch being a detector switch that activates the electronic system.

11. The electronic system of claim 1, further comprising an activation switch being a tactile switch that activates the electronic system.

12. An electronic system connectable to a medication delivery pen and to a needle assembly, the electronic system exchanging data regarding a medicament traveling from the medication delivery pen to the needle assembly, the electronic system comprising:
a hub having a spike that is configured to engage the medication delivery pen and configured to pierce a reservoir septum of the medication delivery pen;
a flow sensor that is in fluid communication with the hub to measure flow data of the medicament;
one or more circuit boards electrically contacting the flow sensor to process and transmit the flow data, the one or more circuit boards include one or more fluid path openings to route a flow of the medicament;
a septum body that is configured to provide fluid communication between the flow sensor and one of a plurality of needles of the needle assembly to administer the medicament to a patient; and
a fluid conduit that transfers the medicament from the flow sensor to the septum body; wherein
a proximal end of the fluid conduit is connected to the flow sensor and a distal end of the fluid conduit is connected to the septum body.

13. An electronic system connectable to a medication delivery pen and to a needle assembly, the electronic system exchanging data regarding a medicament traveling from the medication delivery pen to the needle assembly, the electronic system comprising:
a hub having a spike that is configured to engage the medication delivery pen and configured to pierce a reservoir septum of the medication delivery pen;
a flow sensor that is in fluid communication with the hub to measure flow data of the medicament;
one or more circuit boards electrically contacting the flow sensor to process and transmit the flow data, the one or more circuit boards include one or more fluid path openings to route a flow of the medicament;
a septum body that is configured to provide fluid communication between the flow sensor and one of a plurality of needles of the needle assembly to administer the medicament to a patient; and
a fluid conduit that transfers the medicament from the flow sensor to the septum body; wherein
the septum body includes a recess at its proximal end, and the fluid conduit is disposed in the recess.

14. An electronic system connectable to a medication delivery pen and to a needle assembly, the electronic system exchanging data regarding a medicament traveling from the medication delivery pen to the needle assembly, the electronic system comprising:
a hub having a spike that is configured to engage the medication delivery pen and configured to pierce a reservoir septum of the medication delivery pen;
a flow sensor that is in fluid communication with the hub to measure flow data of the medicament;
one or more circuit boards electrically contacting the flow sensor to process and transmit the flow data, the one or more circuit boards includes one or more LEDs to indicate device status and one or more fluid path openings to route a flow of the medicament;
a septum body that is configured to provide fluid communication between the flow sensor and one of a plurality of needles of the needle assembly to administer the medicament to a patient; and
a diffuser ring that illuminates to indicate device status, wherein
the one or more LEDs project light of different colors to illuminate the diffuser ring; and
the one or more LEDs are disposed at a distal end of the one or more circuit boards.

15. An electronic system connectable to a medication delivery pen and to a needle assembly, the electronic system exchanging data regarding a medicament traveling from the medication delivery pen to the needle assembly, the electronic system comprising:
a hub having a spike that is configured to engage the medication delivery pen and configured to pierce a reservoir septum of the medication delivery pen;
a flow sensor that is in fluid communication with the hub to measure flow data of the medicament;
one or more circuit boards electrically contacting the flow sensor to process and transmit the flow data, the one or more circuit boards include one or more fluid path openings to route a flow of the medicament;
a septum body that is configured to provide fluid communication between the flow sensor and one of a plurality of needles of the needle assembly to administer the medicament to a patient; and
a diffuser ring that illuminates to indicate device status, wherein
the diffuser ring is disposed below the one or more circuit boards.

16. An electronic system connectable to a medication delivery pen and to a needle assembly, the electronic system exchanging data regarding a medicament traveling from the medication delivery pen to the needle assembly, the electronic system comprising:
a hub having a spike that is configured to engage the medication delivery pen and configured to pierce a reservoir septum of the medication delivery pen;
a flow sensor that is in fluid communication with the hub to measure flow data of the medicament;
one or more circuit boards electrically contacting the flow sensor to process and transmit the flow data, the one or more circuit boards include one or more fluid path openings to route a flow of the medicament; and
a septum body that is configured to provide fluid communication between the flow sensor and one of a plurality of needles of the needle assembly to administer the medicament to a patient; wherein
the one or more circuit boards include a snap on member to secure to a diffuser ring.

17. The electronic system of claim 16, wherein
the snap on member is fixed to the diffuser ring to secure the diffuser ring to the one or more circuit boards.

18. A method of operating an electronic system connectable to a medication delivery pen and to a needle assembly, the electronic system exchanging data regarding a medicament traveling from the medication delivery pen to the needle assembly, the method comprising:

piercing a reservoir septum of the medication delivery pen with a spike enclosed in a hub, connecting the medication delivery pen to the hub;

providing fluid communication between the spike and a flow sensor to measure flow data of the medicament;

processing and transmitting the flow data from the flow sensor to a circuit board; and routing medicament flow from the flow sensor, through the circuit board and to a septum body for delivery of the medicament to a patient when connected to the needle assembly; wherein the flow of the medicament does not contact the circuit board.

19. An apparatus including a needle assembly and an electronic system connectable to a medication delivery pen and to the needle assembly, the electronic system exchanging data regarding a medicament traveling from the medication delivery pen to the needle assembly, the apparatus comprising:

the needle assembly comprising a plurality of needles; and the electronic system comprising:
  a hub having a spike that is configured to engage the medication delivery pen and configured to pierce a reservoir septum of the medication delivery pen;
  a flow sensor that is in fluid communication with the hub to measure flow data of the medicament;
  one or more circuit boards electrically contacting the flow sensor to process and transmit the flow data, the one or more circuit boards include one or more fluid path openings to route a flow of the medicament; and
  a septum body that is configured to provide fluid communication between the flow sensor and one of the plurality of needles of the needle assembly to administer the medicament to a patient; wherein the flow of the medicament does not contact the one or more circuit boards.

* * * * *